US012778988B2

(12) United States Patent
Shikanov

(10) Patent No.: US 12,778,988 B2
(45) Date of Patent: Nov. 3, 2026

(54) IMMUNOISOLATION DEVICE

(71) Applicant: THE REGENTS OF THE UNIVERSITY OF MICHIGAN, Ann Arbor, MI (US)

(72) Inventor: Ariella Shikanov, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 502 days.

(21) Appl. No.: 18/463,999

(22) Filed: Sep. 8, 2023

(65) Prior Publication Data

US 2024/0091273 A1 Mar. 21, 2024

Related U.S. Application Data

(63) Continuation of application No. 17/146,089, filed on Jan. 11, 2021, now Pat. No. 11,786,560, which is a continuation of application No. 15/755,242, filed as application No. PCT/US2016/048673 on Aug. 25, 2016, now Pat. No. 10,918,673.

(60) Provisional application No. 62/211,175, filed on Aug. 28, 2015.

(51) Int. Cl.

| | |
|---|---|
| ***A61K 35/54*** | (2015.01) |
| ***A61K 9/00*** | (2006.01) |
| ***A61K 9/06*** | (2006.01) |
| ***A61K 9/48*** | (2006.01) |
| ***A61K 9/50*** | (2006.01) |
| ***A61K 31/565*** | (2006.01) |
| ***A61K 31/57*** | (2006.01) |
| ***A61K 47/10*** | (2017.01) |
| ***A61P 15/08*** | (2006.01) |

(52) U.S. Cl.

CPC ............ *A61K 35/54* (2013.01); *A61K 9/0024* (2013.01); *A61K 9/06* (2013.01); *A61K 9/48* (2013.01); *A61K 9/4816* (2013.01); *A61K 9/50* (2013.01); *A61K 31/565* (2013.01); *A61K 31/57* (2013.01); *A61K 47/10* (2013.01); *A61P 15/08* (2018.01)

(58) Field of Classification Search

CPC ........ A61K 35/54; A61K 9/0024; A61K 9/06; A61K 9/48; A61K 9/4816; A61K 9/50; A61K 31/565; A61K 31/57; A61K 47/10; A61P 15/08

See application file for complete search history.

(56) References Cited

U.S. PATENT DOCUMENTS

| | | | |
|---|---|---|---|
| 6,632,446 | B1 | 10/2003 | Hubbell et al. |
| 6,893,871 | B2 | 5/2005 | Bald et al. |
| 10,918,673 | B2 | 2/2021 | Shikanov et al. |
| 2003/0166833 | A1 | 9/2003 | Lutolf et al. |
| 2009/0004238 | A1 | 1/2009 | Scharp et al. |
| 2012/0142069 | A1 | 6/2012 | Shea et al. |
| 2012/0213708 | A1 | 8/2012 | Anderson et al. |
| 2014/0271843 | A1 | 9/2014 | Ma et al. |

FOREIGN PATENT DOCUMENTS

| | | | |
|---|---|---|---|
| WO | WO2008108736 | A1 | 9/2008 |
| WO | WO2017040200 | A1 | 3/2017 |

OTHER PUBLICATIONS

Anderson et al., (2011) The performance of human mesenchymal stem cells encapsulated in cell-degradable polymer-peptide hydrogels. Biomaterials, 32(14): 3564-3574 (Year: 2011).*

Life in the Lab Staff. Consider humidity in your CO2 incubator for excellent cell growth. ThermoFisher Scientific, Jul. 2024 [retrieved Jan. 7, 2026]. Retrieved from the Internet: https://www.thermofisher.com/blog/life-in-the-lab/consider-humidity-for-excellent-cell-growth/ (Year: 2024).*

Aerts et al., "Xenotransplantation by injection of a suspension of isolated preantral ovarian follicles and stroma cells under the kidney capsule of nude mice." Fertil Steril. Jul. 2010;94(2):708-14.

Anckaert et al., "Culture of oocytes and risk of imprinting defects." Hum Reprod Update. Jan.-Feb. 2013;19(1):52-66.

Binette et al., "Porcine endogenous retroviral nucleic acid in peripheral tissues is associated with migration of porcine cells post islet transplant." Am J Transplant. Jul. 2004;4(7):1051-60.

Ceccarelli et al., "Sculpting the blank slate: how fibrin's support of vascularization can inspire biomaterial design." Acta Biomater. Apr. 2014;10(4):1515-23.

Chiareilli et al., "Early menopause and infertility in females after treatment for childhood cancer diagnosed in 1964-1988 in Ontario, Canada." Am J Epidemiol. Aug. 1, 1999;150(3):245-54.

Chou et al., "Treatment of osteoporosis with TheraCyte-encapsulated parathyroid cells: a study in a rat model." Osteoporos Int. 2006;17(6):936-41.

Divasta et al., "Hormone replacement therapy for the adolescent patient." Ann N Y Acad Sci. 2008;1135:204-11.

Dolmans et al., "Reimplantation of cryopreserved ovarian tissue from patients with acute lymphoblastic leukemia is potentially unsafe." Blood. Oct. 21, 2010;116(16):2908-14.

Dolmans et al., "Risk of transferring malignant cells with transplanted frozen-thawed ovarian tissue." Fertil Steril. May 2013;99(6):1514-22.

(Continued)

*Primary Examiner* — Kara D Johnson

(74) *Attorney, Agent, or Firm* — Casimir Jones, SC; Thomas A. Isenbarger

(57) ABSTRACT

Provided herein is technology relating to immunoisolation of cells and tissues, including, but not exclusively, to compositions, methods, and kits for encapsulating cells and/or tissues within an immunoisolating device to protect the cells/or tissues from host immune rejection.

22 Claims, 20 Drawing Sheets

Specification includes a Sequence Listing.

(56) References Cited

OTHER PUBLICATIONS

Donnez et al., "Restoration of ovarian activity and pregnancy after transplantation of cryopreserved ovarian tissue: a review of 60 cases of reimplantation." Fertil Steril. May 2013;99(6):1503-13.
Elliott et al., "Transplantation of micro- and macroencapsulated piglet islets into mice and monkeys." Transplant Proc. Jan.-Feb. 2005;37(1):466-9.
Garcia "PEG-maleimide hydrogels for protein and cell delivery in regenerative medicine." Ann Biomed Eng. Feb. 2014;42(2):312-22.
Garkavenko et al., "Xenotransplantation of neonatal porcine liver cells." Transplant Proc. Jan.-Feb. 2005;37(1):477-80.
Gibly et al., "Advancing islet transplantation: from engraftment to the immune response." Diabetologia. Oct. 2011;54(10):2494-505.
Giedd et al., "Puberty-related influences on brain development." Mol Cell Endocrinol. Jul. 25, 2006;254-255:154-62.
Gorrill et al., "Pharmacology of estrogens and estrogen-induced effects on nonreproductive organs and systems." J Reprod Med. Sep. 1986;31(9 Suppl):842-7.
Gosden "Restitution of fertility in sterilized mice by transferring primordial ovarian follicles." Hum Reprod. Jul. 1990;5(5):499-504.
Hao et al., "Visible light cured thiol-vinyl hydrogels with tunable degradation for 3D cell culture." Acta Biomater. Jan. 2014;10(1):104-14.
Hershlag et al., "Part 2: Ovarian failure in adolescent cancer survivors should be treated." J Pediatr Adolesc Gynecol. Apr. 2011;24(2):101-3.
Hudson et al., "Age-dependent changes in health status in the Childhood Cancer Survivor cohort." J Clin Oncol. Feb. 10, 2015;33(5):479-91.
Krupetsky et al., "Retroviral packaging cells encapsulated in TheraCyte immunoisolation devices enable long-term in vivo gene delivery." Front Biosci. May 1, 2003;8:a94-101.
Laronda et al., "Initiation of puberty in mice following decellularized ovary transplant." Biomaterials. May 2015;50:20-9. doi.
Lee et al., "Human beta-cell precursors mature into functional insulin-producing cells in an immunoisolation device: implications for diabetes cell therapies." Transplantation. Apr. 15, 2009;87(7):983-91.
Li, et al., "Activation of dormant ovarian follicles to generate mature eggs" PNAS, 107(22) 2010; 10280-10284.
Louie et al., "Cell-based gene therapy experiments in murine experimental autoimmune encephalomyelitis." Gene Ther. Jul. 2005;12(14):1145-53.
Lutolf et al., "Synthetic biomaterials as instructive extracellular microenvironments for morphogenesis in tissue engineering." Nat Biotechnol. Jan. 2005;23(1):47-55.
Mariotto et al., "Survivors of childhood cancer in the United States: prevalence and burden of morbidity." Cancer Epidemiol Biomarkers Prev. Apr. 2015;24(4):653-63.
Mariotto et al., "Long-term survivors of childhood cancers in the United States." Cancer Epidemiol Biomarkers Prev. Apr. 2009;18(4):1033-40.
Meirow et al., "Searching for evidence of disease and malignant cell contamination in ovarian tissue stored from hematologic cancer patients." Hum Reprod. May 2008;23(5):1007-13.
Nieman et al., "Fertility preservation and adolescent cancer patients: lessons from adult survivors of childhood cancer and their parents." Cancer Treat Res. 2007;138:201-17.
Nottola et al., "Cryopreservation and xenotransplantation of human ovarian tissue: an ultrastructural study." Fertil Steril. Jul. 2008;90(1):23-32.
Oktay et al., "Isolation and characterization of primordial follicles from fresh and cryopreserved human ovarian tissue." Fertil Steril. Mar. 1997;67(3):481-6.
Oktay et al., "Cryopreservation of immature human oocytes and ovarian tissue: an emerging technology?" Fertil Steril. Jan. 1998;69(1):1-7.
Rao et al., "Matrix composition regulates three-dimensional network formation by endothelial cells and mesenchymal stem cells in collagen/fibrin materials." Angiogenesis. Jun. 2012;15(2):253-64.
Robison et al., "Survivors of childhood and adolescent cancer: life-long risks and responsibilities." Nat Rev Cancer. Jan. 2014;14(1):61-70.
Shikanov et al., "Hydrogel network design using multifunctional macromers to coordinate tissue maturation in ovarian follicle culture." Biomaterials. Apr. 2011;32(10):2524-31.
Shikanov et al., "Fibrin encapsulation and vascular endothelial growth factor delivery promotes ovarian graft survival in mice." Tissue Eng Part A. Dec. 2011;17(23-24):3095-104.
Smith et al., "Designing follicle-environment interactions with biomaterials." Cancer Treat Res. 2010;156:11-24.
Sorenby et al., "Preimplantation of an immunoprotective device can lower the curative dose of islets to that of free islet transplantation: studies in a rodent model." Transplantation. Jul. 27, 2008;86(2):364-6.
Sweet et al.,"Treatment of diabetic rats with encapsulated islets." J Cell Mol Med. Dec. 2008;12(6B):2644-50.
Tagler et al., "Embryonic fibroblasts enable the culture of primary ovarian follicles within alginate hydrogels." Tissue Eng Part A. Jun. 2012;18(11-12):1229-38.
Tarantal et al., "Real-time bioluminescence imaging of macroencapsulated fibroblasts reveals allograft protection in rhesus monkeys (*Macaca mulatta*)." Transplantation. Jul. 15, 2009;88(1):38-41.
Tibell et al., "Survival of macroencapsulated allogeneic parathyroid tissue one year after transplantation in nonimmunosuppressed humans." Cell Transplant. 2001;10(7):591-9.
Thibaud et al., "Ovarian function after bone marrow transplantation during childhood." Bone Marrow Transplant. Feb. 1998;21(3):287-90.
Waring et al., "Subfertility following treatment for childhood cancer." Hosp Med. Aug. 2000;61(8):550-7.
Weber et al., "Multifunctional pancreatic islet encapsulation barriers achieved via multilayer PEG hydrogels." Cell Transplant. 2008;16(10):1049-57.
Yanay et al., "Long-term erythropoietin gene expression from transduced cells in bioisolator devices." Hum Gene Ther. Nov. 20, 2003;14(17):1587-93.
Yang et al., "Survival of pancreatic islet xenografts in NOD mice with the theracyte device." Transplant Proc. Dec. 2002;34(8):3349-50.
Zhao et al., "Soluble factor(s) from bone marrow cells can rescue lethally irradiated mice by protecting endogenous hematopoietic stem cells." Exp Hematol. Apr. 2005;33(4):428-34.
Zhu "Bioactive modification of poly(ethylene glycol) hydrogels for tissue engineering." Biomaterials. Jun. 2010;31(17):4639-56.
International Search Report of parent application PCT/US2016/048673, mailed Jan. 17, 2017, 17 pages.

* cited by examiner

Figure 1
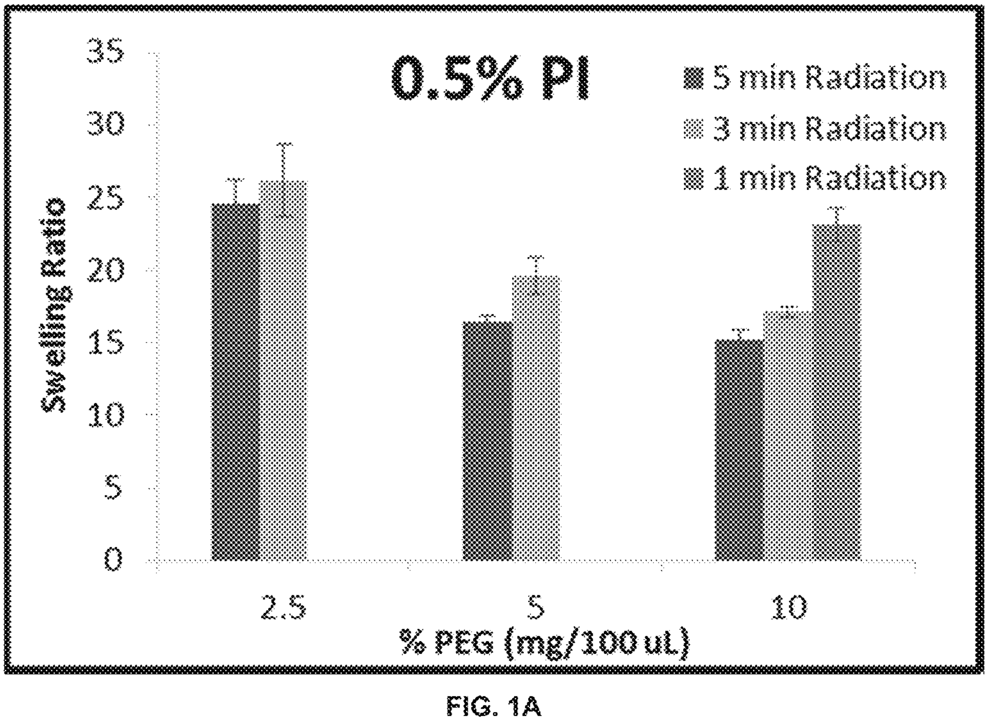
FIG. 1A
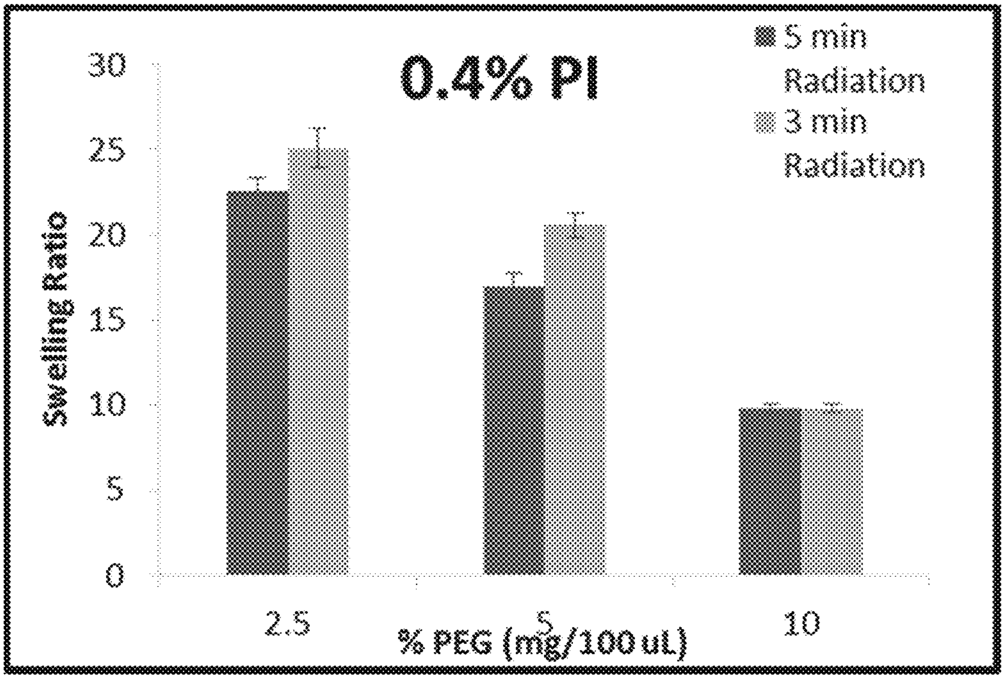
FIG. 1B

Figure 1 (cont.)
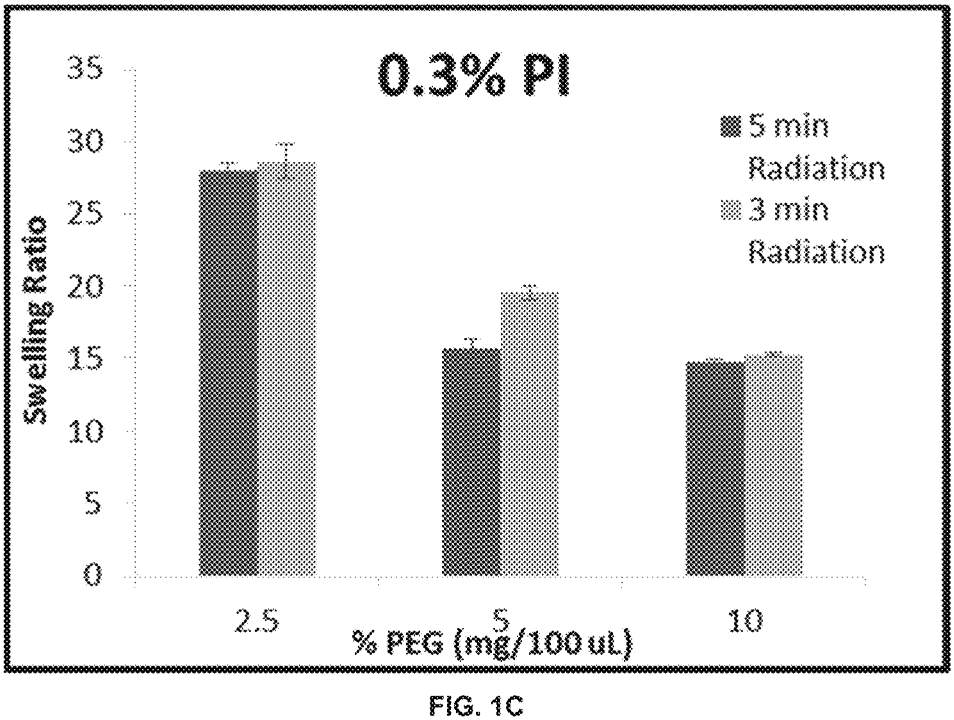
FIG. 1C
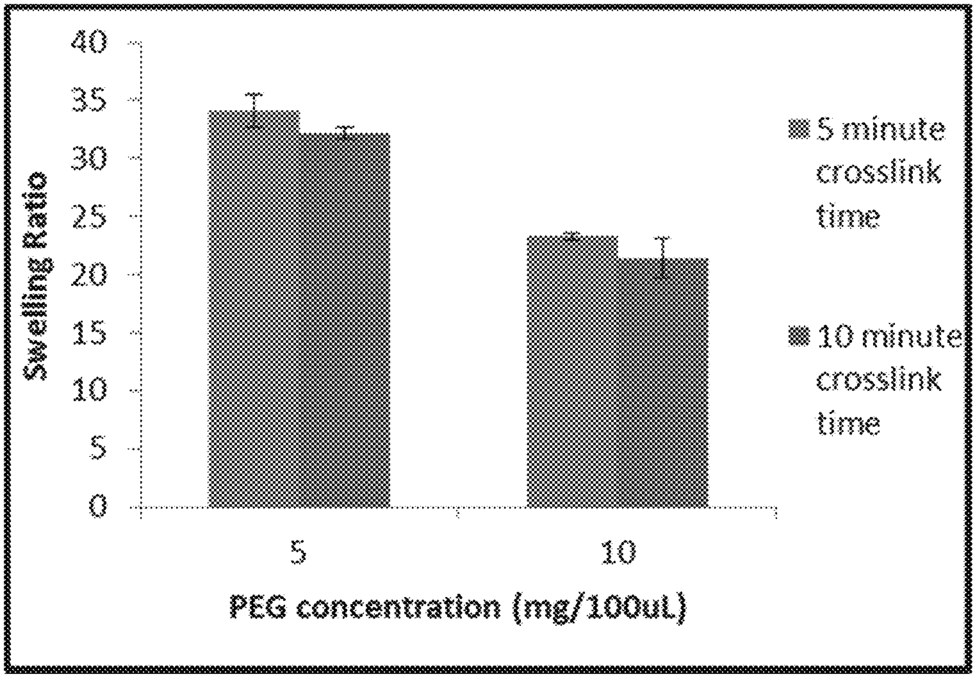
FIG. 1D

Figure 3
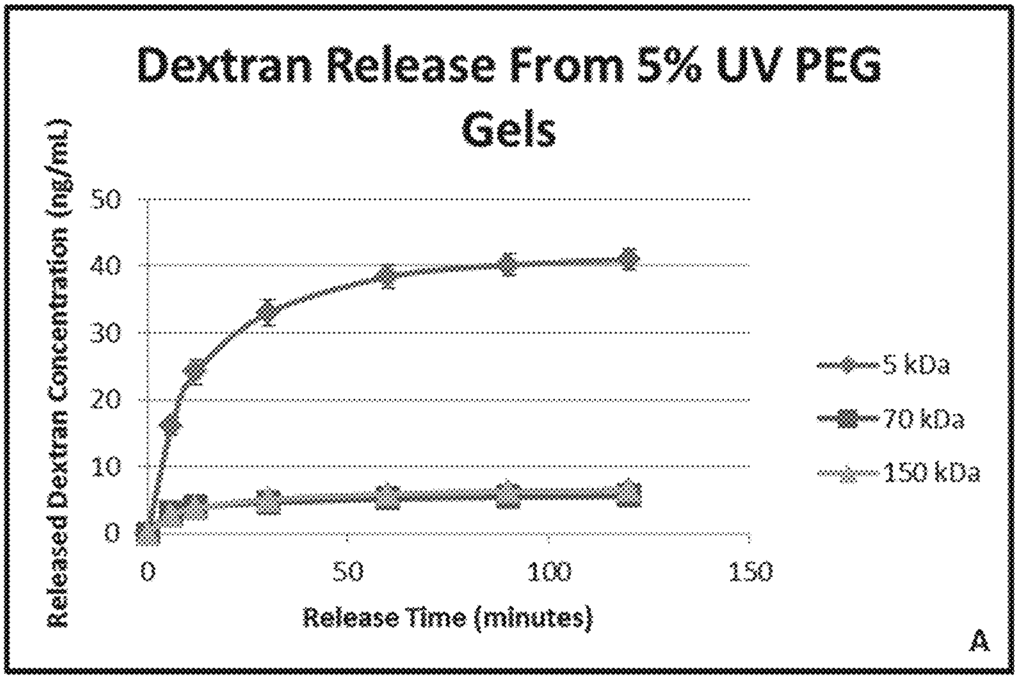
FIG. 3A
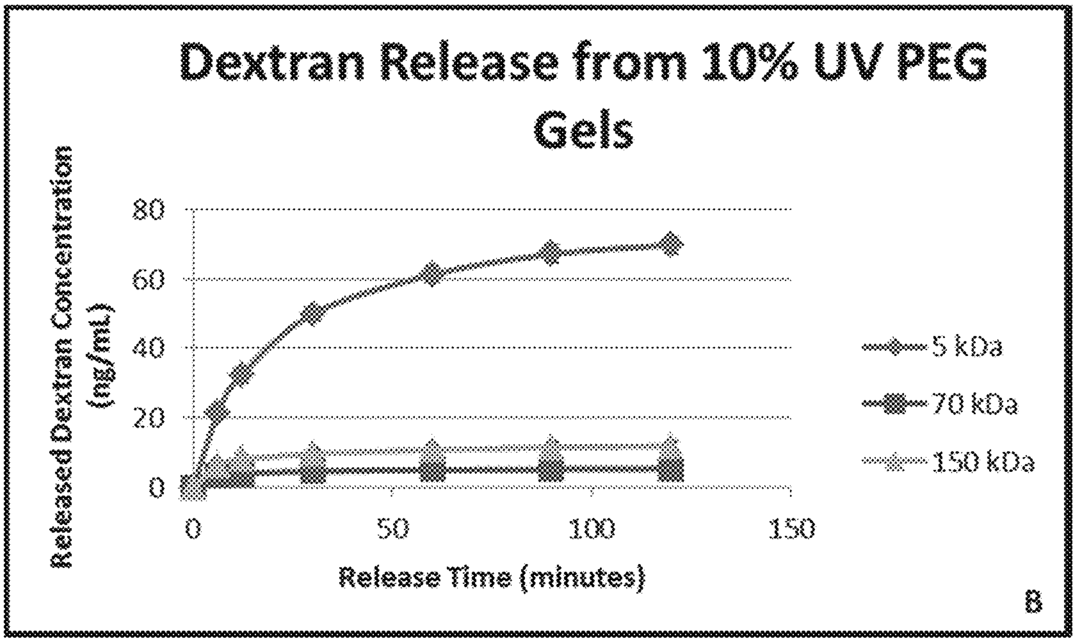
FIG. 3B

Figure 13
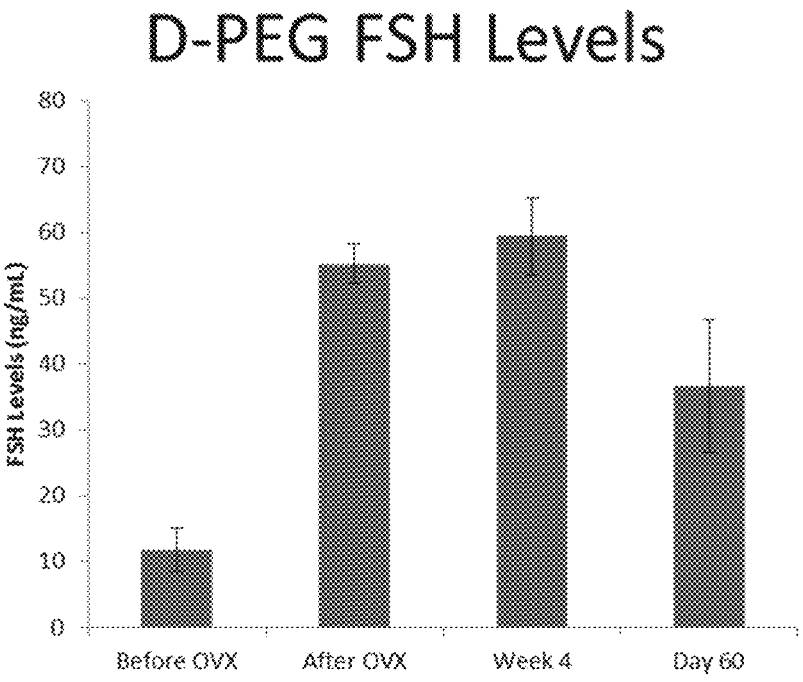
FIG. 13A
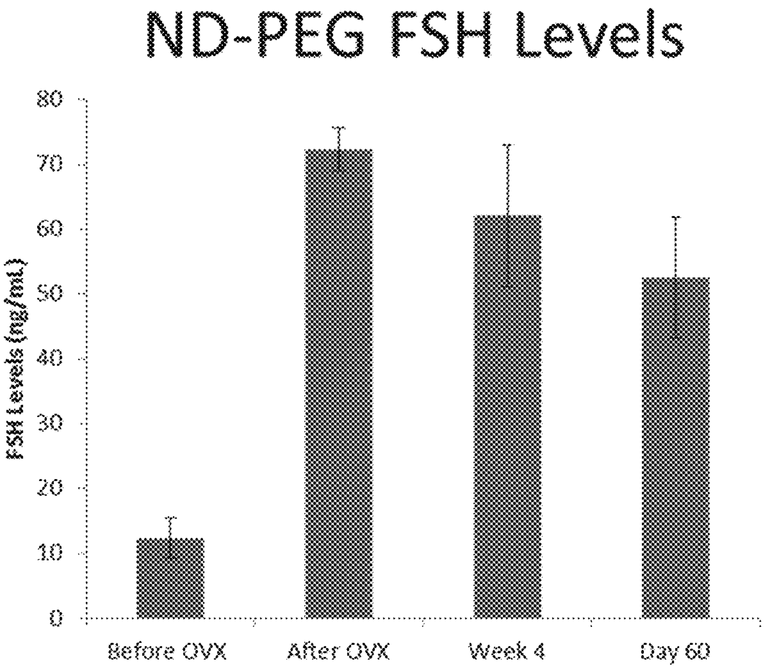
FIG. 13B

Figure 14
D-PEG
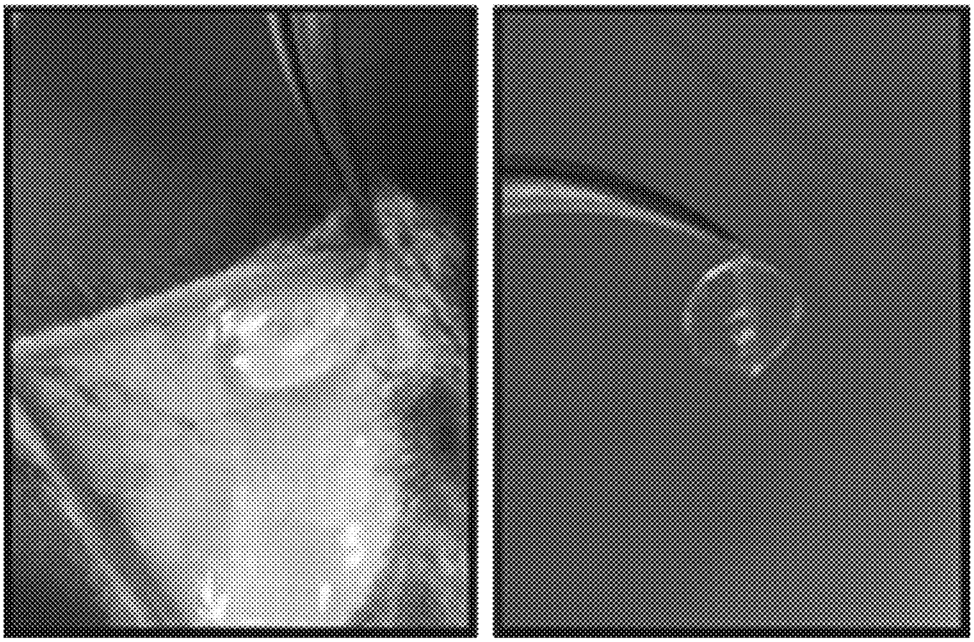
FIG. 14A
D-PEG
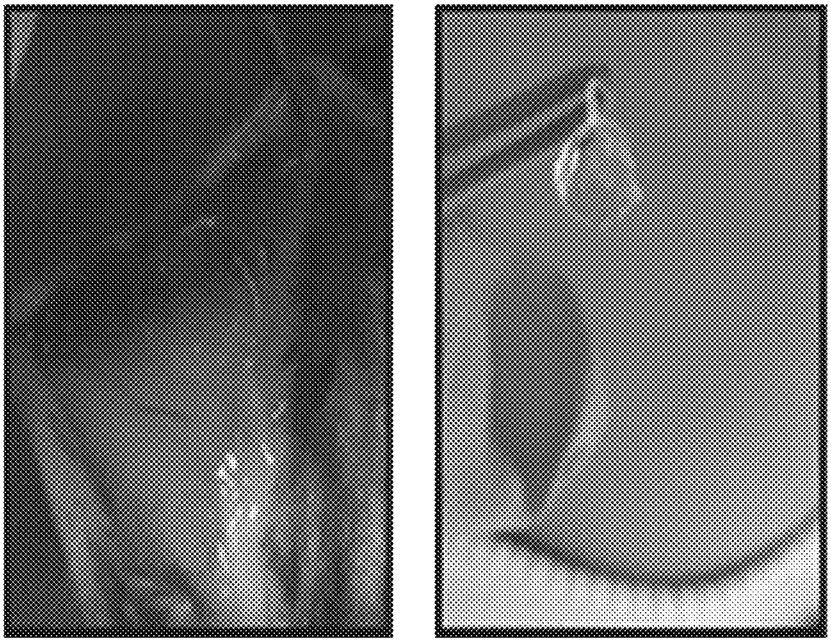
FIG. 14B

Figure 15
FIG. 15A
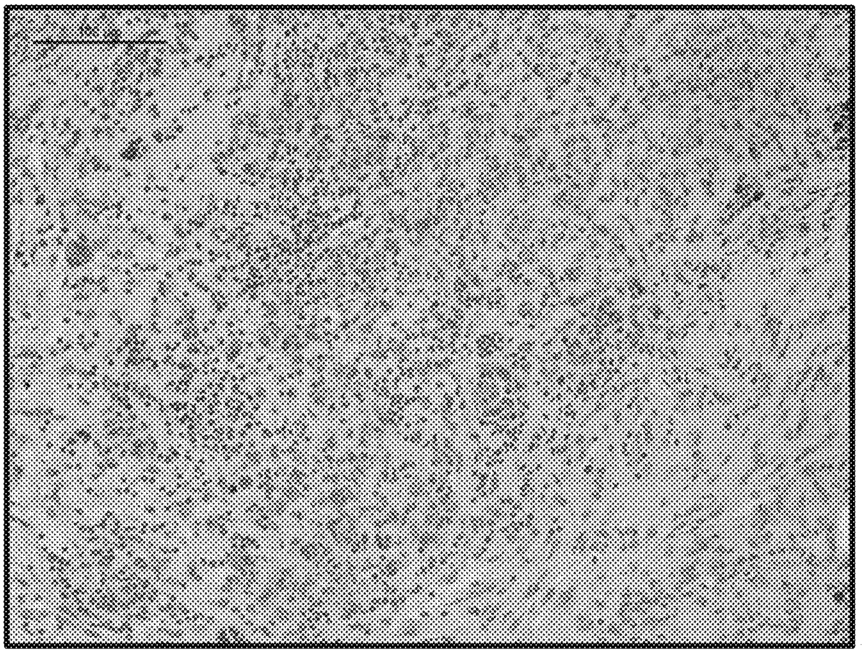
FIG. 15B

Figure 16
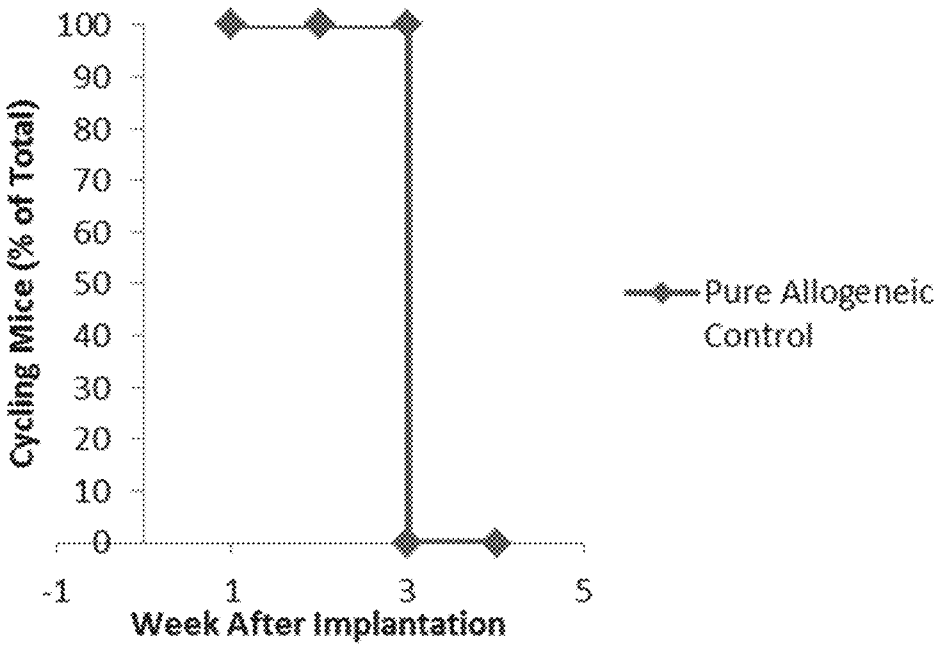
FIG. 16A
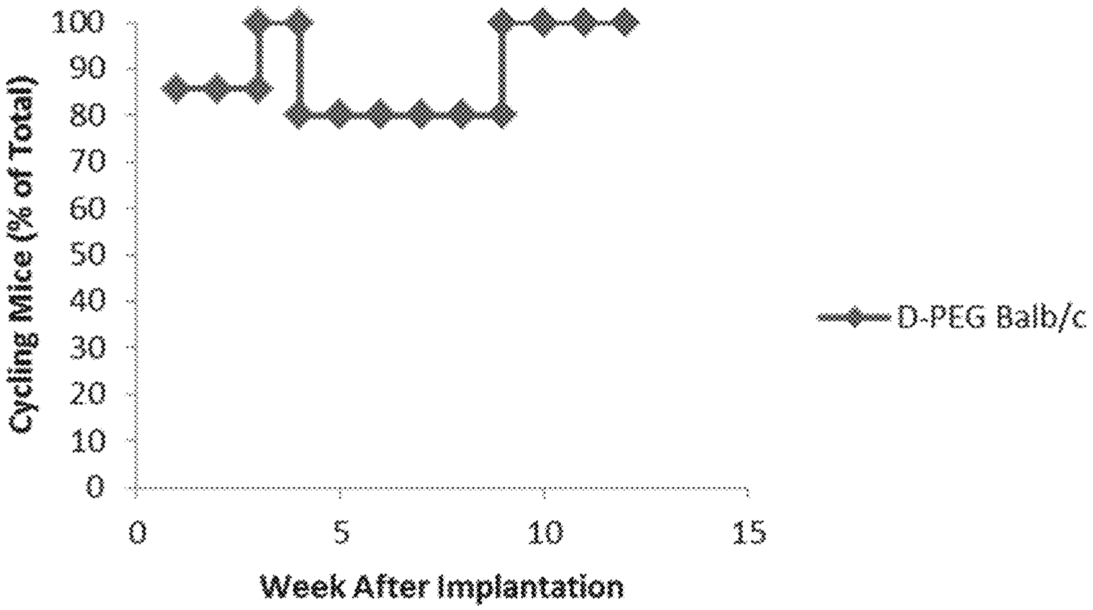
FIG. 16B

Figure 16 (cont.)
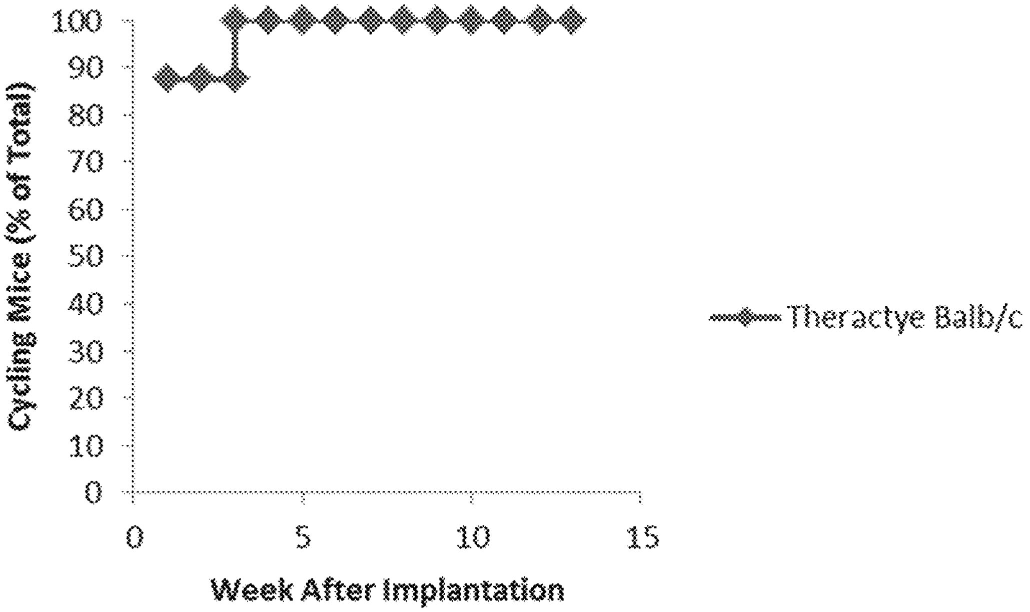
FIG. 16C
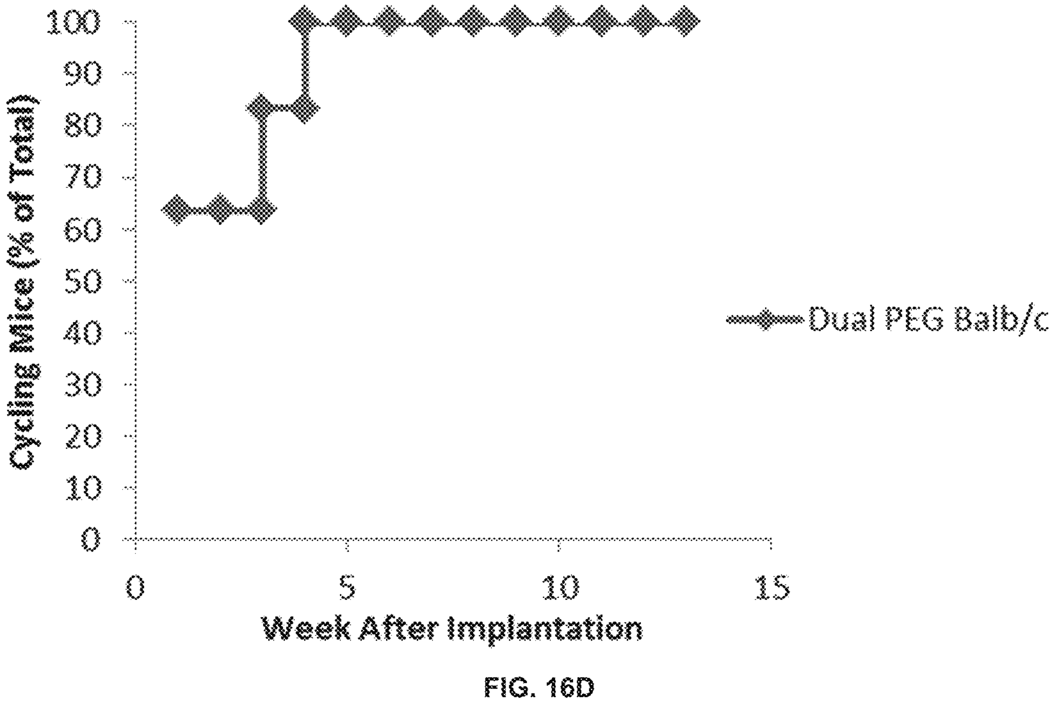
FIG. 16D

IMMUNOISOLATION DEVICE

This application is a continuation of U.S. patent application Ser. No. 17/146,089, filed Jan. 11, 2021, which is a continuation of U.S. patent application Ser. No. 15/755,242, filed Feb. 26, 2018, which is a 371 U.S. National Phase Entry of International Application No. PCT/US2016/048673, filed Aug. 25, 2016, which claims priority to U.S. provisional patent application Ser. No. 62/211,175, filed Aug. 28, 2015, each of which is incorporated herein by reference in its entirety.

SEQUENCE LISTING

The text of the computer readable sequence listing filed herewith, titled "UM-34542-304_SQL", created Sep. 8, 2023, having a file size of 6,042 bytes, is hereby incorporated by reference in its entirety.

FIELD

Provided herein is technology relating to immunoisolation of cells and tissues, including, but not exclusively, to compositions, methods, and kits for encapsulating cells and/or tissues within an immunoisolating device to protect the cells/or tissues from host immune rejection.

BACKGROUND

Premature ovarian failure (POF) is a common consequence of cytotoxic treatments, e.g., used to treat cancer and autoimmune disease, due to extreme ovarian toxicity of chemotherapy and bone marrow transplantation (see, e.g., Darlington et al. (1999) *Am J Emdemiol* 150(3): 245-54; Cohen et al. (2011) *J Podiatr Adolesc Gynecol* 24(2): 101-03; Brauner et al. (1998) *Bone Marrow Transplant* 21(3): 287-90; Wallace et al. (2000) *Hosp Med* 61(8): 550-57; Woodruff et al. (2007) *Cancer Treat Res* 138: 201-17). Modern cancer therapy has improved the survival rate to over 80% for children and young adults diagnosed with cancer in the United States, and now these cancer survivors face long-term health problems (see, e.g., Ness at al. (2015) *J Clin Oncol* 33(5): 479-91; Feuer et al. (2009) *Cancer Epidemiol Biomarkers Prev* 18(4): 1033-40; Mariotta et al. (2015) *Cancer Epidemiol Biomarkers Prev* 24(4): 653-63; Hudson et al. (2014) 14(1): 61-70). In female cancer survivors, POF causes sterility and several problems associated with a loss of ovarian endocrine function: premature osteopenia, muscle wasting, and accelerated cardiovascular diseases. These long lasting effects are significant, particularly for young girls reaching puberty. Extant treatment options for POF rely on hormone replacement therapy (HRT), which delivers unregulated, non-physiological levels of estrogen that interfere with growth in peripubertal girls and predisposes recipients to cancer and thrombotic events. However, although these therapies have been extensively studied in menopausal adult women, long-term safety data in children is scant. The risk of synthetic hormones is attributed to unnaturally elevated levels following their administration, as opposed to the normal fluctuating physiologic levels maintained by the finely tuned feedback mechanism provided by healthy ovaries. Further, no alternative form of therapy for POF is available to young girls.

SUMMARY

In some embodiments, provided herein is a technology related to transplant of cells. For example, in some embodiments the technology finds use in the transplant of cells that produce a bioactive molecule into a patient in need of the bioactive molecule. In some embodiments, the technology relates to the transplant of ovarian cells to a female cancer patient. In some embodiments, the technology relates to treatment of menopause and other conditions. That is, in some embodiments, the technology relates to a donor ovarian transplant strategy that provides delivery of natural estrogen at physiologic levels, while simultaneously reestablishing hormonal feedback regulation. The technology provides a bioengineered matrix that supports follicle survival and function, which, in an immune privileged environment, prevents rejection by the recipient while continuing to produce estrogen and progesterone under conditions similar to normal physiologic regulation. In some embodiments, the technology finds use in treating young girls who are forced to endure ovarian failure as the result of cancer treatment strategies. The technology provides for avoiding the deleterious effects of estrogen and progesterone deficiency and risks associated with synthetic hormonal replacement therapy, thus promoting normal development and puberty, and an otherwise healthy life.

The technology provides a regenerative therapy employing aspects of engineering, materials, chemistry, and life sciences to create synthetic constructs to direct tissue regeneration and restoration of biological function. For example, in some embodiments synthetic hydrogels find use, which provide a three-dimensional environment similar to the extracellular matrix (ECM), allow diffusion of nutrients, and can be modified to present many biological functions, e.g., matrix-to-cell adhesion and biodegradation. In some embodiments, fibrin hydrogels find use for transplantation of ovarian tissue or cells, or for transplantation of isolated human follicles. Fibrin gels have an intrinsic bioactivity and provide a physical connectivity for the follicles in a graft and between the graft and the device, both of which contribute to tissue survival. Furthermore, poly(ethyleneglycol) (PEG) is a synthetic multifunctional hydrophilic polymer that is extensively used in biomedical applications and tissue engineering. PEG-based hydrogels are not immunogenic and have biocompatible chemistry within physiological conditions. The baseline biological inertness of biomaterials such as these provides for incorporating custom designed biological moieties that are naturally found in the extra cellular matrix (ECM). For example, in some embodiments integrin binding molecules derived from ECM proteins, such as RGD, YIGSR, IKVAV, and GFOGER peptides, are attached to PEG polymers to provide for cell adhesion to the otherwise inert PEG hydrogel. In some embodiments, the hydrogels are biodegradable, e.g., by proteolytic degradation mechanisms present in the natural ECM. For example, embodiments of the technology comprise hydrogels crosslinked with (or otherwise incorporating) protease sensitive peptides. Some exemplary peptide sequences having protease sensitivity are derived from collagen (e.g., matrix-metalloproteinase (MMP) sensitive sequence) and fibrin (e.g., plasmin sensitive sequences). In some embodiments, protease-sensitive peptides (e.g., comprising a matrix-metalloproteinase (MMP) sensitive sequence or a plasmin sensitive sequence) are incorporated into PEG hydrogels for degradation of the hydrogel, e.g., by the host enzyme activities (see, e.g., Lutolf and Hubbell (2005) "Synthetic biomaterials as instructive extracellular microenvironments for morphogenesis in tissue engineering" *Nat Biotechnol* 23(1): 47-55). In sum, hydrogels provide a three-dimensional environment for the encapsulated cells or tissues (e.g., ovarian follicles), which promotes follicle function and survival in the device.

Some embodiments comprise use of a peptide that is a plasmin sensitive peptide, e.g., for use as a degradable cross-linker in some embodiments of the technology. Some embodiments comprise use of a peptide (e.g., a plasmin-sensitive peptide) that has the amino acid sequence:

(SEQ ID NO: 1)
Ac-GCYK↓NSGCYK↓NSCG

In the amino acid sequence of the plasmin sensitive peptide, the N-terminal acetyl group is added to remove the electrical charge on this terminal. The arrows indicate the protease cleavage sites. That is, embodiments comprise use of a peptide that has an amino acid sequence according to:

(SEQ ID NO: 2)
GCYKNSGCYKNSCG with an N-terminal acetyl group and that is cleaved by a protease (e.g., plasmin) between lysine and asparagine in the sequence, e.g., after the lysine at position 4 and/or after the lysine at position 10.

Some embodiments comprise use of a peptide that is sensitive to both plasmin and MMP proteases, e.g., for use as a degradable cross-linker in some embodiments of the technology. Some embodiments comprise use of a peptide (e.g., a peptide that is both plasmin-sensitive and MMP-sensitive) that has the amino acid sequence:

(SEQ ID NO: 3)
GCRDVPMS↓MRGGDRCGYK↓NSCG

In the amino acid sequence of the peptide that is both plasmin-sensitive and MMP-sensitive, the arrows indicate the protease cleavage sites. That is, embodiments comprise use of a peptide that has an amino acid sequence according to:

(SEQ ID NO: 4)
GCRDVPMSMRGGDRCGYKNSCG that is cleaved by a protease (e.g., plasmin and/or MMP) between serine and methionine in the sequence at positions 8 and 9 and/or between the lysine and asparagine in the sequence at positions 18 and 19. This peptide sequence is sensitive to MMP and plasmin proteases and thus presents a degradable cross-linker for encapsulated tissue and that finds use with several tissue types, e.g., tissues that comprise one or both of a plasmin and/or MMP protease.

Accordingly, in some embodiments the technology provides an immunoisolation device comprising a degradable inner core comprising cells; and a non-degradable outer shell encapsulating the degradable inner core. The technology is not limited in the types of cells provided in the inner core. For example, in some embodiments, the immunoisolation device comprises cells that are from an endocrine organ, e.g., from an ovary. Further, the technology is not limited in the materials that are used to produce the inner core and the outer shell. In some exemplary embodiments, the degradable inner core comprises a polyethylene glycol and, in some embodiments, the non-degradable outer shell comprises a crosslinked polyethylene glycol. Embodiments contemplate various types of crosslinking of the inner core and outer shell; in some embodiments, the degradable inner core comprises a polyethylene glycol crosslinked with a degradable peptide, e.g., a degradable peptide comprising a matrix-metalloproteinase (MMP) sensitive sequence and/or a plasmin sensitive sequence. In some embodiments, the inner core and/or the outer shell comprises a polyethylene glycol hydrogel, e.g., a polyethylene glycol vinyl sulfone hydrogel, e.g., a photo-polymerized polyethylene glycol vinyl sulfone. In some embodiments, the immunoisolation device comprises polyethylene glycol at 2% to 15% (w/v) and/or the outer shell comprises polyethylene glycol at 2% to 15% (w/v), e.g., 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or 15% PEG.

Some embodiments comprise use of a non-degradable PEG, e.g., PEG-maleimide (PEG-Mal). Some embodiments comprise use of a hydrolytically-degradable PEG, e.g., PEG-acrylate (PEG-Ac).

As described herein, embodiments of the immunoisolation device comprise an inner core configured to allow the cells to grow and the outer shell is configured to allow exchange of metabolites with the environment outside the immunoisolation device and to protect the encapsulated cells from immune recognition by the host immune system components outside the immunoisolation device.

In certain embodiments of the immunoisolation device (e.g., embodiments associated with treating a female endocrine deficiency), the immunoisolation device further comprises estrogen and/or progesterone produced by the cells. And, in some embodiments, the immunoisolation device further comprises a drug, e.g., an immunosuppressive drug.

In some embodiments, the immunoisolation device of claim further comprises polyvinylpyrrolidone.

Related embodiments provide a kit comprising a degradable PEG hydrogel precursor solution and a non-degradable PEG hydrogel precursor solution, e.g., a degradable PEG vinyl sulfone hydrogel precursor solution and a non-degradable PEG vinyl sulfone hydrogel precursor solution. Some kit embodiments further comprise a buffer (e.g., HEPES buffer); a photoinitiator; and/or a cross-linker.

Exemplary embodiments comprise a photo-polymerizable and/or photo-polymerized PEG vinyl sulfone system. In some embodiments, the technology relates to a PEG precursor solution comprising 0.01 to 1% photoinitiator (e.g., 0.01, 0.02, 0.03, 0.04, 0.05, 0.1, 0.2, 0.3, 0.4, 0.5%, 0.6, 0.7, 0.8, 0.9, or 1.0% (w/v) photoinitiator). In some embodiments PEG precursor is irradiated (e.g., by ultraviolet light) for 1 to 10 minutes (e.g., 1, 2, 3, 4, 5, 6, 7, 8, 9, or 10 minutes or more). In some embodiments, polymerization is initiated in the presence of polyvinylpyrrolidone (PVP). For example, some embodiments of the technology provide a non-degradable PEG vinyl sulfone system comprising 5% PEG, 0.4% photoinitiator, and 0.1% (v/v) PVP.

Further embodiments provide a method of treating a subject for an endocrine deficiency comprising implanting the immunoisolation device. For example, in some embodiments the cells of the immunoisolation device produce a bioactive material (e.g., a hormone such as estrogen and/or progesterone) for which the subject is deficient. Particular embodiments relate to treatment of a subject. In some embodiments, the subject is a female who was treated for a reproduction cancer as a child. In some embodiments, the subject is a female who is in need of hormone therapy for menopause.

In some embodiments, the technology relates to an immunoisolation device comprising a synthetic membrane, e.g., a bilayer comprising an inner semipermeable membrane made of polytetrofluoroethylene (PTFE) that is laminated to an outer membrane covered by a loose polyester mesh (e.g., commercially available as THERACYTE, TheraCyte, Inc., Laguna Hills, CA) (e.g., a "TheraCyte pouch" or a "TheraCyte bag"). For example, some embodiments relate to devices comprising cells (e.g., endocrine cells, e.g., ovarian cells) placed in a synthetic membrane, e.g., for immunoisolation of the cells, e.g., for transplantation into a host, and methods relating to placing cells (e.g., endocrine cells, e.g., ovarian cells) into a synthetic membrane pouch or bag and methods relating to transplanting the cells (e.g., endocrine cells, e.g., ovarian cells) in the synthetic pouch or bag into a host.

In some embodiments, the technology provided herein provides for the survival and/or growth of transplanted cells in a host. For example, in some embodiments the technology provides for the survival and/or growth of transplanted cells for 1 to 30 days or more (e.g., for a number of days that is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or for more than 30 days).

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1 is series of plots showing the swelling ratio of ND-PEG-VS comprising 0.5%, 0.4%, and 0.3% photoinitiator (FIG. 1A, FIG. 1B, and FIG. 1C, respectively) and 5% D-PEG-VS (FIG. 1D).

FIG. 13A is a bar plot showing FSH levels in mice before ovariectomy, after ovariectomy, and at week 4, and 60 days after implanting ovarian tissue encapsulated in D-PEG.

FIG. 13B is a bar plot showing FSH levels in mice before ovariectomy, after ovariectomy, and at week 4, and 60 days after implanting ovarian tissue encapsulated in ND-PEG.

FIGS. 14A and 14B are macroscopic images showing allogeneic ovarian tissue encapsulated in D-PEG (left images) and retrieved at the time of sacrifice (right images).

FIGS. 15A and 15B are images showing that implantation of allogeneic ovarian tissue without encapsulation results in rejection and elimination of the implanted tissue after 28 days of implantation; analysis of the images indicated that no ovarian follicles at any stage were found in the implanted tissue. The images were acquired at a magnification of 5× (15A) and 20× (15B).

FIG. 16A is a plot of percentage of estrous cycling mice after implantation of allogeneic ovary tissue without encapsulation in an immunoisolation device.

FIG. 16B is a plot of percentage of estrous cycling mice after implantation of allogeneic ovary tissue a D-PEG immunoisolation device.

FIG. 16C is a plot of percentage of estrous cycling mice after implantation of allogeneic ovary tissue in a Theracyte immunoisolation device.

FIG. 16D is a plot of percentage of estrous cycling mice after implantation of allogeneic ovary tissue in a Dual PEG immunoisolation device.

Figure 2:
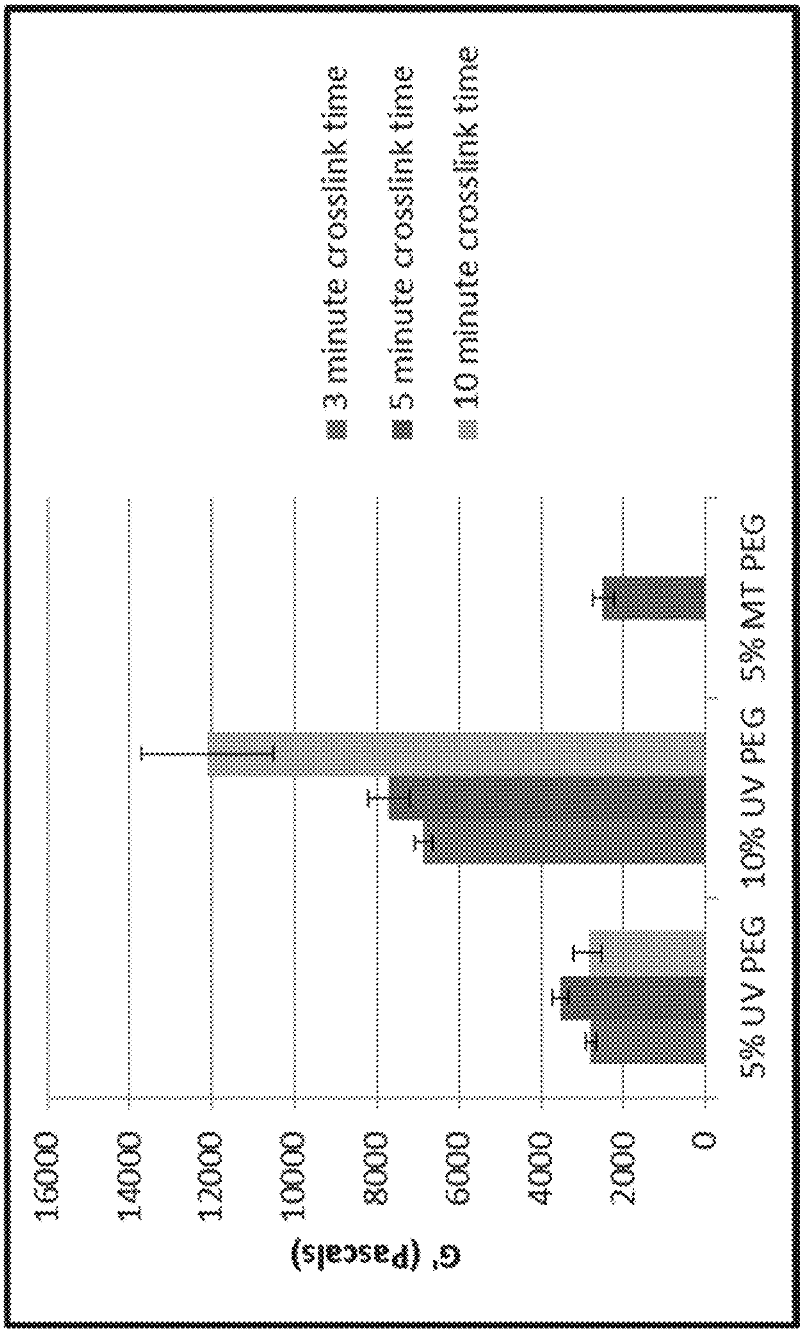
FIG. 2 is a plot showing the measured storage moduli of ND-PEG-VS (at 5% and 10%) and D-PEG-VS (5%).

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is a technology for restoring a biological function (e.g., an endocrine function) in a subject. For example, in some embodiments the technology relates to restoring ovarian function, e.g., in young women with POF or for treating women during menopause. In particular embodiments, the technology relates to transplantation of ovarian tissue with minimized or eliminated host rejection. As described herein, embodiments of the technology provide a dual hydrogel construct that is used to encapsulate transplanted ovarian follicles that secrete sex hormones in the host, e.g., in response to circulating gonadotropins. Accordingly, embodiments of the technology find use in improving (e.g., establishing a normal) physiological endocrine ovarian function in the transplant host.

An allogeneic system to provide endocrine support for ovarian tissue transplantation has yet to be established. While transplantation of ovarian follicles has similarities to transplantation of islet cells to treat diabetes (see, e.g., (Garcia (2014) *Ann Biomed Eng* 42(2): 312-22; Shea et al. (2011) *Diabetologia* 54 (10): 2494-505; Anseth et al. (2008) *Cell Transplant* 16(10): 1049-57)), the transplantation of ovarian follicles is associated with its own set of unique challenges that have not been addressed by previous technologies. Follicles have a similar initial size to islets and secrete sex hormones (estradiol and progesterone) in response to a circulating stimulus. However, unlike islets, follicles expand and contract as they undergo structural and functional changes during the menstrual cycle, which is a feature not supported by static microencapsulation materials. Furthermore, follicles are avascular and relatively resistant to hypoxia, allowing them to survive when implanted as larger structures, which provides an advantage compared to highly vascularized islets. Accordingly, the technology provides a hydrogel that has an immunoisolating exterior ("outer shell") and a degradable core ("inner core") capable of supporting prolonged survival and restoration of endocrine function following allogeneic ovarian transplantation.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control. The section headings used herein are for organizational purposes only and are not to be construed as limiting the described subject matter in any way.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "polymer" means any compound that is made up of two or more monomeric units covalently bonded to each other, where the monomeric units may be the same or different, such that the polymer may be a homopolymer or a heteropolymer. Representative polymers include polyamides (e.g., such as polypeptides), poly-N-substituted glycines (polypeptoids), polysaccharides, polyethylene glycol (PEG), plastics, polynucleotides (e.g., nucleic acids), and the like, where the polymers may be naturally occurring, non-naturally occurring, or synthetic.

As used herein, the term "poly(ethylene glycol)", abbreviated "PEG", refers to a synthetic polymer of ethylene glycol. PEG is water-soluble and can be modified with various functional groups that allow one to tailor its chemistry, physical, and biological properties.

As used herein, the term "polypeptides" includes proteins and fragments thereof (e.g., peptides). In some embodiments, polypeptides are disclosed as amino acid residue (or monomer) sequences. Those sequences are written left to right in the direction from the amino to the carboxy terminus. In accordance with standard nomenclature, amino acid residue sequences are denominated using either a three letter code or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, WT), Tyrosine (Tyr, Y), and Valine (Val, V). In addition, a polypeptide can include non-standard and/or non-naturally occurring amino acids or post-translationally modified amino acids such as hydroxylated amino acids, as well as other amino acids that may be found in phosphorylated proteins in organisms such as, but not limited to, animals, plants, insects, protists, fungi, bacteria, algae, single-cell organisms, and the like. The non-standard amino acids include, but are not limited to, selenocysteine, selenomethionine, pyrrolysine, gamma-aminobutyric acid, carnitine, ornithine, citrulline, homocysteine, hydroxyproline, hydroxylysine, sarcosine, and the like. The non-naturally occurring amino acids include, but are not limited to, trans-3-methylproline, 2,4-methanoproline, cis-4-hydroxyproline, trans-4-hydroxyproline, N-methylglycine or other N-substituted glycines, beta-amino acids, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine.

As used herein, the term "polynucleotide" generally refers to any polyribonucleotide or polydeoxyribonucleotide, which may be unmodified RNA or DNA or modified RNA or DNA. Thus, for instance, the term "polynucleotide" as used herein refers to, among others, single-stranded and double-stranded DNA, DNA that is a mixture of single-stranded and double-stranded regions, single-stranded and double-stranded RNA, and RNA that is a mixture of single-stranded and double-stranded regions, hybrid molecules comprising DNA and RNA that may be single-stranded or, more typically, double-stranded or a mixture of single-stranded and double-stranded regions. The term "polynucleotide" encompasses the terms "nucleic acid", "nucleic acid sequence", and "oligonucleotide". In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term "polynucleotide" includes nucleic acids that comprise one or more modified bases. Thus, nucleic acids with backbones modified for stability or for other reasons are "polynucleotides" as that term is intended herein. Moreover, nucleic acids comprising unusual bases, such as inosine, or modified bases, such as tritylated bases, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including simple and complex cells.

As used herein, the terms "treatment", "treating", and "treat" refer to acting upon a disease (e.g., cancer), disorder, or condition (e.g., biological deficiency or discomfort, e.g., one or more symptoms of menopause) with an agent to reduce or ameliorate the pharmacologic and/or physiologic effects of the disease, disorder, or condition and/or its symptoms. "Treatment," as used herein, covers any treatment of a disease, disorder, or condition in a host (e.g., a mammal, typically a human or non-human animal of veterinary interest), and includes: (a) reducing the risk of occurrence of a disease, disorder, or condition in a subject determined to be predisposed to the disease, disorder, or condition, but not yet diagnosed as having the disease, disorder, or condition; (b) impeding the development of a disease, disorder, or condition; (c) relieving a disease, disorder, or condition, e.g., causing regression of the disease, disorder, or condition and/or relieving one or more symptoms of the disease, disorder, or condition; (d) ameliorating, reducing, or reversing one or more symptoms of a disease, disorder, or condition and/or ameliorating, reducing, or reversing one or more symptoms resulting from a treatment for the disease, disorder, or condition; and (e) providing or restoring normal (or near normal, adequate, sufficient, essentially normal, and/or effectively normal) or improved biological processes in a subject, e.g., a subject who has impaired or damaged biological processes due to a disease, disorder, or condition and/or from treatment of a disease, disorder, or condition. "Treatment" is also meant to encompass providing a pharmacologic effect in a normal subject or in a subject in the absence of a disease, disorder, or condition. For example, "treatment" encompasses providing for improved, enhanced, or desirable effects in the subject (e.g., reduction of tumor load, reduction of symptoms, improved or normal growth and development, extension of a period of a patient's apparent, functional health, etc.).

As used herein, the terms "prophylactically treat" or "prophylactically treating" refers to completely or partially preventing a disease or symptom thereof and/or may be therapeutic in terms of a partial or complete cure for a disease and/or adverse effect attributable to the disease.

The term "attached" or the phrases "interacts with" and "associated with" refers to a stable physical, biological, biochemical, and/or chemical association. In general, association can be chemical bonding (e.g., covalently or ionically), a biological interaction, a biochemical interaction, and in some instances a physical interaction. The association can be a covalent bond, a non-covalent bond, an ionic bond, a metal ion chelation interaction, as well as moieties being linked through interactions such as, but not limited to, hydrophobic interactions, hydrophilic interactions such as hydrogel bonding, charge-charge interactions, n-stacking interactions, combinations thereof, and like interactions.

The term "cancer", as used herein, shall be given its ordinary meaning, as a general term for diseases in which abnormal cells divide without control and form cancer or neoplastic cells, tissues, or tumors. The term cancer can include cancer cells and/or precancerous cells. In particular, and in the context of the embodiments of the present disclosure, cancer refers to ovarian cancer and cancers of the female reproductive organs and system. Cancer cells can invade nearby tissues and can spread through the bloodstream and lymphatic system to other parts of the body. There are several main types of cancer, for example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled, and coordinated unit, a tumor may be formed. Generally, a solid tumor is an abnormal mass of tissue that usually does not contain cysts or liquid areas (although some brain tumors do have cysts and central necrotic areas filled with liquid). A single tumor may even have different populations of cells within it, with differing processes that have gone awry. Solid tumors may be benign (not cancerous) or malignant (cancerous). Different types of solid tumors are named for the type of cells that form them.

Examples of solid tumors are sarcomas, carcinomas, and lymphomas. Leukemias (cancers of the blood) generally do not form solid tumors.

Representative cancers include, but are not limited to, bladder cancer, breast cancer, colorectal cancer, endometrial cancer, head and neck cancer, leukemia, lung cancer, lymphoma, melanoma, non-small-cell lung cancer, ovarian cancer, prostate cancer, testicular cancer, uterine cancer, cervical cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms's tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

A tumor can be classified as malignant or benign. In both cases, there is an abnormal aggregation and proliferation of cells. In the case of a malignant tumor, these cells behave more aggressively, acquiring properties of increased invasiveness.

Ultimately, the tumor cells may even gain the ability to break away from the microscopic environment in which they originated, spread to another area of the body (with a very different environment, not normally conducive to their growth), and continue their rapid growth and division in this new location. This is called metastasis. Once malignant cells have metastasized, achieving a cure is more difficult. Benign tumors have less of a tendency to invade and are less likely to metastasize.

As used herein "administration" refers to introducing a compound into a subject.

As used herein, the term "subject", "host", or "organism" includes humans and mammals (e.g., cats, dogs, horses, etc.). In some embodiments, subjects are mammals, particularly primates, especially humans. For veterinary applications, a wide variety of subjects is suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

As used herein, the term "hydrogel" refers to a substance formed when an organic polymer (natural or synthetic) is cross-linked via covalent, ionic, or hydrogen bonds to create a three-dimensional open-lattice structure that entraps water molecules to form a gel. As used herein, the term "biocompatible hydrogel" refers to a polymer that forms a gel that is not toxic to living cells and allows sufficient diffusion of oxygen and nutrients to entrapped cells to maintain viability.

As used herein, the term "biocompatible" generally refers to a material and any metabolites or degradation products thereof that are generally non-toxic to the recipient and do not cause any significant adverse effects to the subject.

As used herein, phosphate buffered saline, abbreviated "PBS", and Dulbecco's phosphate buffered saline, abbreviated "DPBS", are buffered salines used in biological studies. PBS and DPBS are used in research involving cells. The ion concentration and osmolarity of PBS and DPBS are isotonic, that is, compatible with the human body. In some embodiments, these buffers provide and preserve a stable pH of 7.2-7.6. There is no significant difference between PBS and DPBS. Both of them contain sodium phosphate, sodium chloride, and, when required, potassium phosphate and potassium chloride. In some embodiments, preparations of PBS or DPBS may or may not contain calcium and magnesium. PBS and DPBS have numerous applications because they are not noxious to cells. Both PBS and DPBS can be used to rinse instruments or containers contaminated with cells. Also, both of them can be used in diluting substances.

As used herein, the terms "degradable" and "biodegradable" generally refer to a material that degrades or erodes by hydrolysis or enzymatic action under physiologic conditions to smaller units or chemical species that are capable of being metabolized, eliminated, or excreted by the subject.

As used herein, the "degradation rate" refers to a rate relating the number of smaller units or chemical species that are produced by biodegradation or degradation of a material as a function of time.

As used herein, the "degradation time" refers to the time required to produce a threshold number of smaller units or chemical species by biodegradation or degradation of a material and is a function of polymer composition and morphology.

As used herein, the term "non-degradable" refers to a material that is not "degradable" or that is substantially or effectively less degradable than a degradable material (e.g., has a substantially or effectively lower degradation rate or a substantially or effectively longer degradation time).

As used herein, the term "mammalian cell" refers to any cell derived from a mammalian subject suitable for transplantation into the same or a different subject. The cell may be syngeneic, xenogeneic, autologous, or allogeneic. The cell can be a primary cell obtained directly from a mammalian subject. The cell may also be a cell derived from the culture and expansion of a cell obtained from a subject. For example, the cell may be a stem cell. Immortalized cells are also included within this definition. In some embodiments, the cell has been genetically engineered to express a recombinant protein and/or nucleic acid.

As used herein, the term "transplant" refers to the transfer of a cell, tissue, or organ to a subject from another source. The term is not limited to a particular mode of transfer. Encapsulated cells may be transplanted by any suitable method, such as by injection or surgical implantation.

As used herein, the term "autologous" refers to a transplanted biological substance taken from the same individual.

As used herein, the term "xenogeneic" refers to a transplanted biological substance taken from a different species. As used herein, the term "xenogeneic transplantation" refers to the transplantation of living cells, tissues, or organs from one species to another. Such cells, tissues, or organs are called "xenografts" or "xenotransplants". Both allotransplantation (e.g., a same-species transplant) and xenotransplantation can cause rejection of the graft because the immune system of the host recognizes the transplant as foreign (e.g., as "non-self"). In addition to rejection, disease transmission ("xenozoonosis") and permanent alteration to the host genetic code are causes for concern. Accordingly, the use of immunoisolating devices provides a technology to prevent, eliminate, and/or minimize rejection of a graft and/or to prevent, eliminate, and/or minimize the risk of disease transmission.

As used herein, the term "allogeneic" refers to a transplanted biological substance taken from a different individual of the same species. Accordingly, as used herein, the term "allogeneic transplantation" or "allotransplantation" refers to the transplantation (e.g., of a cell, tissue, or organ) to a recipient from a genetically non-identical donor of the same species. The transplant is called an allograft, allogeneic transplant, or homograft. Most human tissue and organ transplants are allografts because humans genetically differ from each other. Similarly, transplantation of a tissue between different strains of mice is termed an allogeneic transplantation. An immune response against an allograft, termed rejection, will arise in healthy individuals without immune suppression.

As used herein, the term "isogeneic transplantation" or "syngraft" is a graft between genetically identical individuals, typically between identical twins or between animals of a single highly inbred strain. This type of graft typically does not provoke the immune system and does not cause rejection.

As used herein, the term "endocrine system" refers to the collection of cells and tissues of an organism that secrete hormones directly into the blood to control physiological and behavioral activities of the organism. The endocrine system comprises a series of glands that produce molecules called hormones. A number of glands that signal to each other in a sequence are usually referred to as an axis, for example, the hypothalamic-pituitary-gonadal (HPG) axis that in a female connects the glands involved in regulating the ovarian function. Reproductive endocrine function is mediated by sex hormones, such as estradiol and progesterone. Besides the effect of the sex hormones on the reproductive organ, they have other functions, such as metabolism, fat storage, blood vessel and skin maintenance, protein synthesis, prevention of bone resorption, and muscle degeneration.

As used herein, the term "endogenous" as it relates to an organism or biological system refers to a substance, molecule, etc. produced or synthesized within the organism or biological system.

As used herein, the term "endogenous hormones" as it relates to an organism or biological system refers to hormones produced or synthesized within the organism or biological system. For example, in females estradiol is produced in special structures called ovarian follicles. Follicles produce estradiol in response to other hormones that regulate ovarian function.

As used herein, the terms "epiphyses" and "epiphyseal growth plate" refer to features of a bone. Bone is a living tissue comprising a protein (collagen) matrix upon which calcium salts are deposited. A growing bone is described by the ends, or epiphyses, and the shaft. The portion of each epiphysis in contact with the shaft is a plate of actively proliferating cartilage (connective tissue composed of collagen and other fibrous proteins) called the epiphyseal growth plate. Linear growth of the shaft can continue as long as the epiphyseal growth plates exist, but cease when the growth plates are converted to bone as a result of hormonal influences at puberty. This is known as epiphyseal closure and occurs at different times in different bones.

As used herein, the term "estrogen" refers to a class of steroid hormones secreted by the ovaries. For example, estradiol is a predominant estrogen in the plasma. Estradiol is produced and secreted from ovaries and it plays a key role in puberty, providing a hormonal milieu for physical and psychosocial development. Estradiol is responsible for the development of the female appearance, bone growth, and brain development. Simultaneously, increases in estradiol levels during puberty stimulate other growth hormones that lead to the pubertal growth spurt. The hypothalamus, pituitary gland, and the ovary interact along the "HPG axis". The pulsatile release of Gonadotropin Releasing Hormone (GnRH) from the hypothalamus stimulates the secretion of Luteinizing hormone (LH) and Follicle stimulating hormone (FSH) from the pituitary gland in the brain. FSH directly stimulates granulosa cells in the growing follicles to secrete estradiol. LH stimulates theca cells in the follicle to produce precursors of estradiol to increase its production. HPG axis is a loop that is tightly regulated by the secreted hormones.

As used herein, the term "exogenous" as it relates to an organism or biological system refers to a substance, molecule, etc. originating from outside an organism or biological system.

As used herein, the term "exogenous hormone" as it relates to an organism or biological system refers to a hormone originating from outside the organism or biological system. Exogenous estrogen is a synthetic analog of the estradiol and can mimic the function of endogenous estradiol.

As used herein, the term "follicle" or "ovarian follicle" refers to the functional unit of the ovary. It contains a germ cell that is future to develop into an egg, surrounded by multiple layers of supportive cells, called granulosa cells. In the ovaries, granulosa cells synthesize and secrete estradiol in response to the hormones that control the ovarian function. Theca cells build the outside layer of the follicle. Theca cells produce androgens, which are the precursors for estradiol produced by granulosa cells.

As used herein, the term "follicular stimulating hormone", abbreviated "FSH", refers to a hormone that is secreted from the pituitary gland as a result of hypothalamus stimulation. FSH acts on ovaries and stimulates estradiol secretion and follicle growth.

As used herein, the term "folliculogenesis" refers to a process that describes the maturation of the ovarian follicle, a densely packed shell of somatic cells that surround a germ cell. Folliculogenesis describes the progression of small immature follicles to a mature follicle ready for ovulation. Hormones secreted from hypothalamus (GnRH) and pituitary gland (FSH and LH) regulate the process of follicle development. In response to hormonal stimulation follicles produce estradiol and progesterone that regulate the hormone production in the brain in a series of positive and negative feedback mechanisms. The levels of all hormones in the HPG axis cyclically fluctuate.

As used herein, the term "gamete" refers to a cell that fuses with another cell during fertilization in organisms that reproduce sexually. In a female, the gamete is as As used herein, the term "germ cell" refers to a cell that gives rise to a female gamete (egg) or a male gamete (sperm).

As used herein, the term "hormone" refers to a substance released from endocrine tissue into the bloodstream where it travels to a target tissue to generate a response. Hormones regulate various human functions, including metabolism, growth and development, tissue function, sleep, and mood. The term hormone as used herein also encompasses natural or synthetic molecules having the same or similar bioactive properties as a hormone released by endocrine tissue; and encompasses derivatives of natural and synthetic hormones and natural and synthetic molecules having the same or similar bioactive properties as a hormone released by endocrine tissue.

As used herein, the term "gonadotropin releasing hormone", abbreviated "GnRH", is the first hormone in the axis between hypothalamus, pituitary gland, and ovary. GnRH stimulates the secretion of the hormones from the pituitary gland (FSH and LH), which in turn control the ovarian function.

As used herein, the term "immunoisolation" or "immune isolation" refers to a strategy used to protect a therapeutic, such as implanted cells or tissue, from being rejected by a donor. By providing a barrier around the implanted cells or tissue, an immunoisolation device allows the passage of nutrients and oxygen into the device to support the survival of implanted cells or tissue and prevents the passage of immune cells and antibodies into the device, thus eliminating or minimizing rejection of the implanted cells or tissue by the host immune system. Immunoisolation of implanted cells or tissue allows foreign grafts to survive for extended, often indefinite intervals.

As used herein, the term "in vitro" refers to an environment outside a living organism. In science this term refers to experiments performed in an artificial or synthetic environment.

As used herein, the term "in vivo" refers to within a living organism. In science this term refers to experiments performed in an animal model or in humans.

As used herein, the term "luteinizing hormone", abbreviated "LH" refers to a hormone that is secreted from the pituitary gland as a result of hypothalamus stimulation. LH acts on theca cells in the follicles to stimulate the production of the precursors of estradiol.

As used herein, the term "primordial follicles" refers to immature and undeveloped stage of the follicles. These follicles contain one germ cell, which is surrounded by several somatic cells. The primordial follicles constitute the majority of the ovarian reserve at any age.

As used herein, the term "thrombosis" refers to the formation of a blood clot ("thrombus") inside a blood vessel, obstructing the flow of blood through the circulatory system. When a thrombus is significantly large enough to reduce the blood flow to a tissue, oxygen deprivation can occur and metabolic products can accumulate. A larger thrombus causing a much greater obstruction to the blood flow may result in anoxia, the complete deprivation of oxygen and tissue death.

As used herein, the term "biological communication" refers to the ability of a biological component to communicate with another biological component, e.g., by exchange of communicating substances such as metabolites, catabolites, proteins, nucleic acids, small molecules (e.g., hormones), lipids, etc. with the biological component. A first biological component in biological communication with a second biological component is exposed to communicating substances produced and/or secreted by the second biological component. As used herein, a "biological component" is not limited by size or scale and thus may be a molecule, biological structure, organelle, cell, tissue, organ, system, or organism.

DESCRIPTION

Transplant rejection is an adaptive immune response that occurs via cellular immunity (mediated by killer T cells) as well as humoral immunity (mediated by activated B cells secreting antibody molecules), along with an innate immune response mediated by phagocytic cells and soluble immune proteins. Cellular immunity protects the body by activating antigen-specific cytotoxic T-lymphocytes that are able to induce apoptosis in body cells displaying epitopes of foreign antigen on their surface, activating macrophages and natural killer cells, and stimulating cells to secrete a variety of cytokines that influence the function of other cells involved in adaptive immune responses and innate immune responses. Accordingly, provided herein is technology for minimizing and/or eliminating rejection of transplanted cells, e.g., ovarian cells.

In some embodiments, the technology comprises use of donor ovarian tissue encapsulated in an immunoisolating device. This technology finds use in improving and/or restoring ovarian endocrine function and controlling host immunity, e.g., to restore ovarian endocrine function, for example, in young women with POF. The technology provides an immunoisolating device that is adapted for the particular characteristics of certain tissue types, e.g., ovarian tissue, and comprises well-characterized biomaterials. Accordingly, the technology provides a new, clinically relevant therapy to improve or restore ovarian endocrine function (e.g., in young women and girls with POF) by improving or restoring a physiological balance of the HPG axis that exists in healthy women, which is difficult to achieve with exogenous pharmacological treatments.

Immunoisolation

Immunoisolation is a technique to protect transplanted tissue from rejection by "hiding" the transplant from the recipient immune system. Immunoisolation approaches include use of semipermeable membranes, microencapsulation, and macroencapsulation technologies to provide for the diffusion of nutrients and small molecules, while preventing free exchange of cells. In some embodiments, semisolid hydrogels find use. In some embodiments, an encapsulation device comprises an inert and durable pouch comprising a semipermeable membrane system.

The field of ovarian tissue transplantation for restoring fertility and ovarian endocrine function in sterile women has progressed. However, a remaining concern relating to safe and ethical autotransplantation in cancer survivors is avoiding the risk of re-introduction of malignant cells, which could lead to recurrence of the primary disease after reimplantation. Multiple research groups have demonstrated that ovarian tissue from leukemia patients is positive for malignant cells in >50% of cases. Hematological malignancies, which contribute to 30% of all childhood cancers, are of particular concern, because leukemia cells can be found in any organ and have the potential to reseed the cancer when the ovarian tissue is transplanted back to the patient. Thus, transplanting the ovarian construct in an immunoisolating device not only protects the follicles from host immune rejection, but also protects the host from potential pathogens and cancer cells entering the body. This approach also extends the pool of potential ovarian tissue donors to xenografts and allografts.

In some embodiments, the technology provides an encapsulation device to provide immune isolation for transplanted cells placed within the encapsulation device, e.g., the technology provides an immunoisolation device. The immunoisolation device allows the cells to exchange hormones, metabolites, catabolites, and other biologically active substances (except immune components) with the body of the host, but protects the transplanted cells from immune recognition and immune rejection by the host.

Encapsulation/Immunoisolation Devices

In some embodiments, the technology relates to encapsulation/immunoisolation devices. For instance, in some embodiments the encapsulating device is a two-layer encapsulating device that comprises an "outer shell" and an "inner core". In particular embodiments, the outer shell of the encapsulating device is prepared with a non-degradable (ND) substance (e.g., a non-degradable hydrogel, e.g., comprising a first PEG (e.g., a PEG crosslinked by exposure to ultraviolet radiation (e.g., crosslinked with a degradable (e.g., proteolytically degradable) crosslinker))) and the inner core is prepared with a degradable substance (e.g., a degradable hydrogel, e.g., comprising a second PEG (e.g., a PEG crosslinked by exposure to ultraviolet radiation)). The non-degradable outer shell of this design provides immune isolation of a therapeutic (e.g., transplanted cells, e.g., transplanted ovary cells) placed within the inner core and, in embodiments in which the therapeutic comprises cells or tissues, the degradable inner core allows the implanted cell or tissue to expand as it grows, e.g., by the secretion of enzymes that degrade the inner core (e.g., proteases).

In some embodiments, the two-layer encapsulating device comprises two poly(ethylene glycol) (PEG) hydrogels, e.g., a first PEG hydrogel that provides a degradable inner core and a second PEG hydrogel that provides a non-degradable outer shell. Therapeutics (e.g., tissue, e.g., ovarian tissue) are implanted in the inner core of embodiments of the two-layer PEG encapsulating devices to provide immunoisolation for the therapeutics implanted within the devices.

In some embodiments, the inner core comprises fibrin (e.g., a degradable fibrin). In some embodiments, the inner core comprises fibrin (e.g., a degradable fibrin) and PEG (e.g., a degradable PEG).

In some embodiments, the inner core further comprises a hormone, e.g., in some embodiments the inner core comprises cells and a hormone. In some embodiments, the inner core comprises ovarian cells and a sex hormone, e.g., a progesterone and/or an estrogen and/or anti-mullerian hormone (AMH). In some embodiments, the inner core comprises estrogen alone, estrogen plus progesterone, or estrogen plus progestin, which is a synthetic hormone with effects similar to those of progesterone. The technology is not limited in the source of the sex hormone, e.g., the source may be a plant, animal, or recombinant organism. The sex hormone may be a bio-identical hormone, a synthetic hormone, or a hormone isolated from a natural source. In some embodiments, the sex hormone is an estropipate, an estradiol, an estrogen, a conjugated estrogen; a medroxyprogesterone; a norethindrone; a drospirenone; a levonorgestrel; a norgestimate; and/or a bazedoxifene.

In some embodiments, the compositions are fabricated into synthetic organs, such as a synthetic ovary containing encapsulated ovarian cells. In some of these embodiments, the cells are encapsulated in a single hydrogel compartment. In other embodiments, the composition contains a plurality of microencapsulated cells dispersed or encapsulated in a biocompatible structure.

In some embodiments, the technology comprises use of PEG and crosslinked PEG (e.g., to produce degradable PEG vinyl sulfone hydrogels, non-degradable PEG vinyl sulfone hydrogels, and dual PEG hydrogels comprising degradable PEG vinyl sulfone hydrogels and non-degradable PEG vinyl sulfone hydrogels, as described below). Crosslinking PEG using ultraviolet light has been used to prepare PEG-based hydrogels. However, some PEG precursors are hydrolytically degradable, such as PEG-acrylate. Thus, while PEG-acrylate readily forms hydrogels upon addition of photo initiators and irradiation, the presence of an ester bond in the polymer backbone makes these hydrogels hydrolytically unstable and degradable when immersed in an aqueous environment, such as a live organism. Some embodiments comprise use of a non-degradable PEG that is PEG-maleimide.

Accordingly, the technology relates to a hydrogel system that is not sensitive to hydrolytic degradation and that is degraded by proteases secreted by live cells (e.g., that is susceptible to a cell-driven (proteolytic) degradation). For example, in some embodiments 4-arm PEG-VS finds use in the technology. However, prior to the development of the technology provided herein, a photo-polymerization protocol for 4-arm PEG-VS had not been developed. Accordingly, the development of the technology provided herein was associated with developing a photo-polymerized PEG-VS system, e.g., by testing varying Irgacure 2959 concentrations (e.g., including but not limited to 0.05, 0.3, 0.4, 0.5% (w/v)), a range of irradiation times, and polymerization in the presence of polyvinylpyrrolidone (PVP). After testing many combinations and performing preliminary characterization experiments, some embodiments of the technology provide a ND-PEG-VS system comprising 5% PEG, 0.4% photoinitiator, and 0.1% (v/v) PVP. Furthermore, development of the technology was associated with developing associated testing methods to characterize the hydrogels and to collect data describing the hydrogels. For example, methods were developed to quantify dextran release from gels by dissolving a dextran in a PEG precursor solution (e.g., at a concentration of 1 mg/ml), gelling the PEG to produce a hydrogel, and then measuring the release of dextran from the hydrogel. During the development of embodiments of the technology, it was discovered that inclusion of dextran hindered gel formation and gels did not form using the aforementioned ND-PEG-VS protocol. Thus, experiments were conducted to develop alternative technologies, e.g., by soaking gels in a dextran solution, e.g., for 24 hours, and then left in D-PBS to quantify dextran release.

In some embodiments, an 8-arm PEG-VS (e.g., a 40 kDa 8-arm PEG-VS) is used for the outer shell (e.g., in some embodiments the outer shell comprises 8-arm PEG-VS (e.g., 40 kDa 8-arm PEG-VS), e.g., cross-linked 8-arm PEG-VS (e.g., cross-linked 40 kDa 8-arm PEG-VS)). In some embodiments, a 4-arm PEG-VS (e.g., a 20 kDa 4-arm PEG-VS) is used for the outer shell (e.g., in some embodiments the outer shell comprises 4-arm PEG-VS (e.g., 20 kDa 4-arm PEG-VS), e.g., cross-linked 4-arm PEG-VS (e.g., 20 kDa 4-arm PEG-VS)). Without being bound by theory, it is contemplated that a lower molecular weight PEG produces a tighter network, further restricting the passage of host immune cells through the outer shell without affecting the exchange of nutrients and hormones.

Polyethylene Glycol (PEG)

PEG hydrogel is a synthetic multifunctional hydrophilic polymer. PEG-based hydrogels are not immunogenic and have biocompatible chemistry within physiological conditions. PEG provides a synthetic matrix that provides for controlling the degradation, stiffness, and pore size characteristics of the encapsulation device. Accordingly, embodiments of the technology comprise the use of polyethylene glycol (PEG). PEG, also known as polyethylene oxide (PEO) or polyoxyethylene (POE), is a polymer of ethylene oxide (e.g., a polyether) and has a molecular formula according to (1) or (2) below:

$$H—(O—CH_2—CH_2)_n—OH \quad (1)$$

$$C_{2n}H_{4n+2}O_{n+1} \quad (2)$$

PEG is a versatile polymer prepared by polymerization of ethylene oxide. Various production methods produce PEG having a wide range of molecular weights (e.g., from 300 g/mol to 10,000,000 g/mol; e.g., from 100 daltons to 100 kilodaltons), chain lengths, and geometries (e.g., linear, branched, star, multi-arm, comb, etc.). In particular, branched PEG has 3 to 10 PEG chains linked to a central core group, star PEG has 10 to 100 PEG chains linked to a central core group, and comb PEG has multiple PEG chains linked to a linear polymer backbone.

The different sizes and geometrical forms of PEG are produced using an initiator to initiate the polymerization of the ethylene oxide monomers. The most common initiator is a monofunctional methyl ether PEG, or methoxypoly(ethylene glycol), abbreviated mPEG. Further, PEG is available in a wide range of purities, e.g., in some embodiments the PEG is a polydisperse PEG having a broad range of molecular weights or lengths or is a polydisperse PEG having a narrow range of molecular weights or lengths. In some embodiments, the PEG is monodisperse (e.g., uniform PEG or discrete PEG), e.g., the PEG has a very high purity, e.g., the PEG has a molecular weight or chain length that is monodisperse, uniform, or discrete. Very high purity PEG is crystalline.

PEG is often described using a number that indicates the average molecular weight of the PEG polymers. For example, a PEG with n=9 would have an average molecular weight of approximately 400 daltons and would be described by the name “PEG 400”. Most PEG preparations comprise molecules with a distribution of molecular weights (e.g., a polydisperse PEG). The size distribution is typically characterized by the weight average molecular weight ($M_w$) and its number average molecular weight ($M_n$), the ratio of which is called the polydispersity index ($M_w/M_n$). $M_w$ and $M_n$ can be measured by mass spectrometry.

PEGylation is the act of covalently coupling a PEG structure to another larger molecule, for example, a therapeutic protein, which is then referred to as a PEGylated protein.

PEG is widely soluble, e.g., in water, methanol, ethanol, acetonitrile, benzene, and dichloromethane, and PEG is insoluble in diethyl ether and hexane.

Accordingly, PEG provides a versatile and “tunable” material for the production of devices described herein. For example, one can control the stiffness, size exclusion properties, and degradability of PEG hydrogels by controlling the PEG concentration, cross-linking, and molecular weight and geometry of the PEG used to form the hydrogels. During the development of embodiments of the technology, experiments were conducted to test the physical characteristics (e.g., permeability to molecules, cells, etc.; stiffness) of PEG hydrogels as a function of PEG concentration (% w/v) and/or extent and type of cross-linking. For example, the technology encompasses PEG hydrogels formed with PEG concentrations of 2% to 15% (e.g., 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, or 15% PEG). Furthermore, the extent of cross-linking can be controlled by controlling the exposure to a source of ultraviolet light (e.g., exposing the PEG precursor solution for 0.5 to 10 minutes, e.g., 0.5 minute, 1 minute, 1.5 minutes, 2 minutes, 2.5 minutes, 3 minutes, 3.5 minutes, 4 minutes, 4.5 minutes, 5 minutes, 5.5 minutes, 6 minutes, 6.5 minutes, 7 minutes, 7.5 minutes, 8 minutes, 8.5 minutes, 9 minutes, 9.5 minutes, or 10 minutes.

According to embodiments of the technology, controlling the PEG concentration provides control of the intrinsic characteristics of the hydrogel, e.g., stiffness, network density, and size exclusion barrier. For example, increasing the PEG concentration (w/v) produces a stiffer gel, a tighter network, and a lower exclusion barrier. Further, according to embodiments of the technology, controlling the extent of cross-linking (e.g., by controlling the cross-linking time) provides control of the intrinsic characteristics of the hydrogel, e.g., stiffness, network density, and size exclusion barrier. For example, increasing the cross-linking (e.g., by increasing the cross-linking time) produces a stiffer gel, tighter network, smaller pores, and lower exclusion barrier.

Some embodiments comprise use of a non-degradable PEG, e.g., PEG-maleimide (PEG-Mal). Some embodiments comprise use of a hydrolytically-degradable PEG, e.g., PEG-acrylate (PEG-Ac).

Anti-Inflammatory, Immunosuppressant, and Anti-Proliferative Drugs

In some embodiments, compositions according to the technology further comprise a drug (e.g., an anti-inflammatory drug, immunosuppressant drug, or an anti-proliferative drug). Drugs suitable for use in the disclosed compositions are described and can be identified using disclosed methods. Representative drugs include glucocorticoids, phenolic antioxidants, anti-proliferative drugs, or combinations thereof. These are collectively referred to herein as “anti-inflammatory drugs” unless stated otherwise.

Non-limiting examples of drugs that find use in embodiments of the disclosed technology include steroidal anti-inflammatories such as dexamethasone, 5-FU, daunomycin, and mitomycin. Anti-angiogenic or anti-proliferative drugs are also useful. Examples include curcumins (e.g., including monoesters and tetrahydrocurcumin) and drugs such as sirolimus (rapamycin), ciclosporin, tacrolimus, doxorubicin, mycophenolic acid, and paclitaxel and derivatives thereof. In some embodiments, the drug is an mTOR inhibitor (e.g., sirolimus and everolimus) or biolimus A9, a highly lipophilic, semisynthetic sirolimus analogue with an alkoxy-alkyl group replacing hydrogen at position 42-O. Lisofylline is a synthetic small molecule with anti-inflammatory properties.

In some embodiments, the drug is a calcineurin inhibitor (e.g., cyclosporine, pimecrolimus, and tacrolimus).

In some embodiments, the drug is a synthetic or natural anti-inflammatory protein. In some embodiments, the device comprises an antibodies specific to select immune components. In some embodiments, the drug is an anti-T cell antibody (e.g., anti-thymocyte globulin or anti-lymphocyte globulin), anti-IL-2R alpha receptor antibody (e.g., basiliximab or daclizumab), or anti-CD20 antibody (e.g., rituximab).

In some embodiments, the devices comprise an immunosuppressant drug, for example, a glucocorticoid, cytostatic, antibody, drug acting on immunophilin, and/or other immunosuppressant drug. In some embodiments, the immunosuppressant inhibits the expression and/or activity of a cytokine (e.g., interleukin 1 (IL-1), IL-2, IL-3, IL-4, IL-5, IL-6, IL-8, and TNF-alpha) and/or the expression and/or activity of a cytokine receptor.

Cells

The technology provides a device to encapsulate cells to protect them from the immune system of a transplant host and allow exchange of non-immune substances (e.g., molecules) between the cells and the host. Thus, the technology provides a device to immunoisolate cells from a host immune system. While particular embodiments described herein relate in particular to the encapsulation and immunoisolation of ovary cells, the technology is not limited with respect to the cells that are incorporated into the immunoisolation device described herein. In embodiments comprising use of ovarian cells, the encapsulated ovarian cells (e.g., mammalian ovarian follicular cells) and/or ovarian follicles are capable of producing and secreting progesterone and 17ß-estradiol analogously to that which occurs in vivo.

Thus, depending on the disorder to be treated, the immunoisolation device can encapsulate any suitable biological material, e.g., cells, tissues, organs or parts of organs, or other biological systems or parts of biological systems. In some embodiments, the biological material is any material that is a capable of being encapsulated within the devices described (e.g., within a membrane pouch or hydrogel). For example, in exemplary embodiments the biological material is cellular material, e.g., cells or groups of cells such as acini, follicles, islets, and the like. Typically, the biological material is a cell or group of cells or tissue that can provide a subject with some therapeutic result when introduced into the subject, for example the release of a bioactive agent. The type of cell(s) will vary depending on the disorder to be treated, as is evident to those skilled in the art. For example, in the treatment of liver failure, hepatocytes are used, and in the treatment of diabetes, pancreatic cells (of one or more types) are used. The cells may be of the same type or a different type than the native tissue at the site of implantation. For example, in the treatment of a neurological disorder in a human, human neuronal cells may be administered, or non-human cells, such as PC12 cells derived from rats, may be administered.

Cells from a variety of sources can be used, including but not limited to autografts (host stem-cell derived; host tissue (e.g., ovarian tissue) removed and preserved (e.g., cryopreserved) prior to treatments (e.g., cytotoxic treatments), allografts (either primary cells or stem-cell derived), xenografts (porcine cells or others), or genetically engineered cells. In some embodiments, human biological material, or biological material derived from humans, finds use for treatment of a human. In some embodiments, biological material from other sources, for example cows, pigs, rats, sharks and sheep, finds use. Such removal may be carried out while the donor is alive or from a dead donor. In embodiments wherein the organs, tissues, or cells are the ovaries, ovarian tissue, or ovarian cells, the ovaries, ovarian tissue, or ovarian cells are appropriately removed and washed in a physiological solution.

Embodiments provide that the biological material is obtained from any suitable source, for example research laboratories, local slaughterhouses, cell cultures, donor tissue, and the like. The number of cells is readily controlled by means known to the skilled practitioner. For example, in some embodiments the density of a cell suspension is varied during formation of immunoisolation device to provide immunoisolation devices with varied numbers of cells encapsulated within.

The cells may be pluripotent, multipotent, totipotent, or differentiated embryonic or adult stem cells; primary differentiated cells; or immortalized cells, among other cell types. In certain embodiments, stem cells comprise, e.g., cells derived from cord blood, amniotic fluid, menstrual blood, placenta, Wharton's jelly, cytotropoblasts, and the like. The cells may also comprise any combination of the above-listed cell types.

In some embodiments, the biological material comprises pancreatic islets, hepatocytes, choroid plexuses, neurons, parathyroid cells, and cells secreting clotting factors. In embodiments for the treatment of diabetes, the cellular material is pancreatic beta cells, pancreatic islets (Islets of Langerhans), or other insulin-producing islets capable of treating a patient suffering from diabetes. In some embodiments for the treatment of a pancreatic exocrine disorder, the cellular material is centroacinar cells, pancreatic basophilic cells, or acini. In embodiments for the treatment of a pituitary disorder, the cellular material is a cell of the anterior pituitary gland.

In some embodiments, the bioactive agent is any agent that is or can be released or secreted from the biological material. For example, pancreatic islets have the capability of secreting the bioactive agent insulin; choroid plexuses have the capability of secreting cerebral fluids; neurons have the capability of secreting agents such as dopamine that can affect the nervous system; and parathyroid cells have the capability of secreting agents that can effect metabolism of calcium and phosphorus in a subject. In some embodiments, the bioactive agent is a hormone or neurotransmitter. In some embodiments for treatment of a pancreatic disorder, the bioactive agent is selected from the group consisting of gastrin, glucagon, insulin, pancreatic polypeptide, and somatostatin. In some embodiments for treatment of a pancreatic disorder, the bioactive agent is selected from the group consisting of chymotrypsin, pancreatic amylase, pancreatic lipase, and trypsin. In embodiments for treatment of a thyroid disorder, the bioactive agent is selected from T1, T2, T3, T4, and calcitonin. In some embodiments for treatment of a neurological disorder, the bioactive agent is a neurotransmitter, and preferably is dopamine.

In some embodiments, the cells comprise ovarian follicles. Follicles are the functional units of the ovary, capable of secreting large amounts of estrogen, androstenedione (the precursor of progesterone), and progesterone. These hormones are synthesized in the somatic cells of the follicle, theca and granulosa, after stimulation with gonadotropins secreted from the pituitary gland in the brain. According to embodiments of the technology, isolated ovarian follicles are encapsulated in an immunoisolation device that supported the volumetric expansion of the growing follicle while maintaining its spherical shape. The culture of the follicles contained all the required nutrients and physiological levels of FSH. The encapsulated follicles expanded during 8 days of culture, which correlated with the increased levels of the secreted hormones.

In some embodiments, somatic cells (e.g., within the follicle) and/or gametes are isolated from the tissues by aspiration, centrifugation of the follicular liquids, or digestion of the intracellular matrix. In some embodiments, following centrifugation, the cellular sediment is washed by repeated passages in culture medium and recovered by removal of the supernatant. Methods are available to quantify the cellular concentration of the sediment, e.g., as determined by direct counting using a Makler chamber, a Bürker chamber, by cytofluorimetry, or by using semi-automated and automated cell counters.

In some embodiments, the isolated organs, tissues, or cells are suspended in culture or maintenance media until their encapsulation, preserving them in an environment at a temperature, in some embodiments, between ambient room temperature and −200° C. and, in some embodiments, at a humidity between 40% and 100%. In some embodiments, the isolated organs, tissues, or cells are suspended in culture or maintenance media until their encapsulation, preserving them in an environment at a temperature between the normal body temperature of the host (e.g., a human having a temperature of approximately 37° C.) and −200° C.

In some embodiments, culture or maintenance media include a physiological solution (isotonic saline), glucosate solution, Basal Medium Eagle (BME) and derivatives thereof, Hanks salts solution and derivatives thereof, tissue culture medium 199 (TCM 199) and derivatives thereof, phosphate buffered saline (PBS) and derivatives thereof, Krebs salts solution and derivatives thereof, Dulbecco modified Eagle's medium (DMEM) and derivatives thereof, tris-buffered medium (TBM) and derivatives thereof, Tyrode's salts solution and derivatives thereof, Modified sperm washing medium, modified human tubal fluid, Modified Ham's F-10 medium, Upgraded B2 INRA medium, B2 INRA Menezo Medium, Upgraded B9 medium, and various other culture media as known and used by those skilled in the art.

In some embodiments, the cells or tissue, suspended in culture medium or follicular liquid, are optionally diluted into a culture medium. In some embodiments, the culture medium comprises a component (e.g., a hydrophilic polymer) that provides a synthetic extracellular matrix. In some embodiments, dilution is between 1:0.05 and 1:200, e.g., between 1:0.1 to 1:100.

In some embodiments, the cell type chosen for encapsulation in the disclosed compositions is chosen to provide a desired therapeutic effect. Embodiments provide that the cells may be from the patient (autologous cells), from another donor of the same species (allogeneic cells), from another species (xenogeneic), or mixtures thereof. In some embodiments, the technology comprises use of anti-inflammatory and/or immunomodulatory (e.g., immunosuppressive) drugs to reduce the immune response, e.g., provoked by the presence of the foreign hydrogel materials or due to the trauma of the transplant surgery. Cells can be obtained from biopsy or excision of the patient or a donor, cell culture, or cadavers. In some embodiments, cells are obtained from a culture.

In some embodiments, cells are stem cells, e.g., induced pluripotent stem cells from the subject, mobilized stem cells, mesenchymal stem cells (MSCs), etc.

In some embodiments, cells are reproductive cells, endocrine cells (e.g., ovarian cells), nervous system cells, growth factor-secreting cells, bone marrow cells, epithelial cells, endothelial cells, and/or genetically engineered cells, among other cell types.

In some embodiments, the cells secrete a therapeutically effective substance, such as a protein, nucleic acid, or small molecule (e.g., a hormone). In some embodiments, the cells metabolize toxic substances. In some embodiments, the cells form structural tissues, such as skin, bone, cartilage, blood vessels, or muscle. In some embodiments, the cells are natural, such as ovarian cells that naturally secrete hormones. In some embodiments, the cells are genetically engineered to express a heterologous protein or nucleic acid and/or to overexpress an endogenous protein or nucleic acid.

Bioactive Agents

In some embodiments, bioactive agents delivered to a host by cells of the immunoisolation device include, e.g., insulin, glucagon, erythropoietin; Factor VIII; Factor IX; hemoglobin; albumin; neurotransmitters such as dopamine, gamma-aminobutyric acid (GABA), glutamic acid, serotonin, norepinephrine, epinephrine, and acetylcholine; growth factors such as nerve growth factor (NGF), brain-derived neurotrophic factor (BDNF), neurotrophin-3 (NT-3), neurotrophin 4/5 (NT-4/5), ciliary neurotrophic factor (CNTF), glial cell line-derived neurotrophic factor (GDNF), cholinergic differentiation factor/leukemia inhibitory factor (CDF/LIF), epidermal growth factor (EGF), insulin-like growth factor (IGF), fibroblast growth factor (FGF), and platelet-derived growth factor (PDGF); pain inhibitors such as Substance P, catecholamines, dynorphins, endorphins, or enkephalins; hormones such as sex hormones (e.g., estrogen, progesterone), parathyroid hormone, or growth hormone; immunomodulators such as granulocyte-macrophage colony stimulating factor (GM-CSF); neuromodulators; lymphokines; cytokines; cofactors; antibodies; aptamers; and enzymes.

Mouse Model of Infertility

Embodiments of the technology were tested using a mouse model of infertility. In this model, both ovaries are surgically removed in a young female mouse (4-16 weeks old). As a result, estrogen production decreases and FSH levels increase because of the lack of the negative feedback of estrogen on pituitary gland. To test embodiments of the encapsulation device, the same female receives an ovarian transplant and the endocrine function is monitored for a predetermined time period. During the development of embodiments of the technology, encapsulated ovarian cells were tested in this model.

Kits

Some embodiments provide kits for the preparation of immunoisolated cells in dual layer PEG devices according to the technology. For example, in some embodiments kits comprise previously prepared, pre-measured, and pre-packaged raw materials (e.g., degradable PEG vinyl sulfone hydrogel precursor solution; non-degradable PEG vinyl sulfone hydrogel precursor solution; optionally, a buffer (e.g., HEPES buffer); a photoinitiator; and/or cross-linker (e.g., a peptide, e.g., a plasmin sensitive cross-linker peptide)). Some embodiments of kits further comprise an ultraviolet light source as well as appropriate disposable, sterile, non-sterile, and/or sterilizable materials. The preparation of the encapsulation devices and/or encapsulation devices comprising cells is performed by placing cells, tissues, tissue parts, organs, organ parts, cell cores, gametes, and/or embryos into the encapsulation device according to the technology provided herein. The cells, tissues, tissue parts, organs, organ parts, cell cores, gametes, and/or embryos may be freshly removed and/or appropriately preserved according to the techniques known to those skilled in the art.

Uses

While not limited in the uses and applications of the technology provided herein, the technology finds use in some embodiments to treat a patient who is in need of a bioactive substance that is produced and/or secreted by cells, e.g., cells encapsulated in the immunoisolation devices described herein.

The various embodiments have a wide variety of therapeutic and prophylactic uses in the area of cell therapy or cellular transplantation, for example in the treatment of age-related disorders, allergic disorders, autoimmune diseases, cancers, endocrine disorders, immune disorders, inflammatory disorders, neurological disorders, organ failure, proliferative disorders, other conditions involving tissue injury, and other conditions wherein replacement cells are desirable.

As known in the art, cell therapy is the transplantation of human or animal cells to replace or repair damaged or malfunctioning tissues, and/or cells. The types of cells that are administered correspond in some way with the organ or tissue in the patient that is failing. For example, in the context of a subject suffering from diabetes or related disorders, cell therapy treatment involves the transplantation of insulin-producing cells that can replicate the function of pancreatic cells and release insulin into the subject upon the advent of certain conditions, namely an elevated glucose level in the subject. In the context of a subject suffering from impaired endocrine function (e.g., impaired sex hormone function, e.g., impaired ovarian function), cell therapy includes transplantation of hormone producing cells (e.g., ovarian cells).

For example, in some embodiments, the technology finds use in treating a patient (e.g., a female patient) who has been treated for a cancer, e.g., a cancer of the reproductive system. In some embodiments, the technology finds use for menopause hormone therapy of adult women.

In some embodiments, the technology finds use in treating a subject who has endured an accident or an injury, e.g., the technology finds use in wound healing. In some embodiments, the device is used for transplanting a graft such as a layer or layers of cultivated, autologous, allogenic, and/or xenogenic cells to cover an accidental or surgical wound.

In some embodiments, the technology finds use in treating a subject who is transgender or who has transitioned gender.

In some embodiments, the technology finds use in treating an autoimmune disease.

In some embodiments, the technology finds use in treating an adverse drug reaction in a subject.

In some embodiments, the technology finds use in treating a developmental defect.

Exemplary endocrine disorders that are treated by various embodiments of the present technology include, but are not limited to: adrenal disorders, including but not limited to adrenal insufficiencies such as Addison's disease, congenital adrenal hyperplasia (adrenogenital syndrome), and mineralocorticoid deficiency, Conn's syndrome, Cushing's syndrome, and pheochromocytoma; autoimmune polyendocrine syndromes, including but not limited to Type 1 autoimmune polyendocrine syndrome, Type 2 autoimmune polyendocrine syndrome (Schmidt's syndrome), and immunodysregulation polyendocrinopathy enteropathy X-linked syndrome (IPEX or XPID); glucose homeostasis disorders, including but not limited to diabetes mellitus, hypoglycemia, and idiopathic hypoglycemia; metabolic bone diseases, including but not limited to osteoporosis, osteitis deformans (Paget's disease of bone), rickets and osteomalacia; pancreatic disorders, including but not limited to diabetes mellitus, exocrine pancreatic insufficiency, hypoglycemia, pancreatitis, and Shwachman-Diamond Syndrome; parathyroid gland disorders, including but not limited to primary hyperparathyroidism, secondary hyperparathyroidism, tertiary hyperparathyroidism, hypoparathyroidism, and pseudohypoparathyroidism; pituitary gland disorders, including but not limited to diabetes insipidus, growth hormone deficiency, hypopituitarism (or panhypopituitarism), Sheehan syndrome, and syndrome of inappropriate antidiuretic hormone; sex hormone disorders, including but not limited to amenorrhea, infertility, hypogonadism, gonadotropin deficiency, Kallmann syndrome, Klinefelter syndrome, menopause, menstrual function disorders, ovarian failure, polycystic ovary syndrome, testicular failure, and Turner syndrome; and thyroid disorders, including but not limited to hyperthyroidism, hypothyroidism, and thyroiditis, for example acute thyroiditis, De Quervain thyroiditis, Graves-Basedow disease, Hashimoto's thyroiditis, Hashitoxicosis, iatrogenic hyperthyroidism, iatrogenic hypothyroidism, Ord's thyroiditis, postoperative hypothyroidism, postpartum thyroiditis, silent thyroiditis, thyroid storm, toxic nodular struma (Plummer's disease), and toxic thyroid nodule.

Exemplary cancers (e.g., of the endocrine organs) that are treated by various embodiments of the present technology include, but are not limited to: adrenal hyperplasia or neoplasia, adrenocortical carcinoma, insulinoma, pituitary tumors such as pituitary adenomas, prolactinoma (or hyperprolactinemia), acromegaly (gigantism), and Cushing's disease, thyroid tumors such as thyroid adenoma, anaplastic thyroid cancer, follicular thyroid cancer, medullary thyroid cancer, and papillary thyroid cancer, and endocrine tumor syndromes such as Carney Complex, McCune-Albright syndrome, von Hippel Lindau syndrome (VHL syndrome), and multiple endocrine neoplasia (multiple endocrine adenomatosis) or MEN syndromes such as Wermer syndrome (MEN 1), Sipple syndrome (MEN 2A), MEN 2B, and FMTC.

It is contemplated that the technology finds use to implant cells that produce endogenous hormones or other factors at physiological levels in response to a stimulator. For example, in some embodiments the technology finds use in treating Diabetes Type I and II by delivering islets that produce and secrete insulin in response to glucose levels in the blood. In some embodiments, the technology finds use in delivering cells that produce and secrete growth hormone to treat disorders affecting the pituitary gland and production of growth hormone. In some embodiments, induced pluripotent cells derived from the patient (e.g., autologous cells) or donor stem cells (e.g., allogeneic cells) are differentiated into particular cell types (e.g., ovarian cells) and delivered to a host (e.g., transplanted) in the device.

In some embodiments, the technology finds use for the implantation of thyroid or parathyroid tissue in a subject to treat conditions associated with hypoparathyroidism or hypothyroidism.

In some embodiments, the technology finds use for the implantation of liver cells in a subject, e.g., to treat acute liver failure. In exemplary embodiments, the implanted cells metabolize toxic metabolites, such as ammonia, and secrete urea, which is removed from the body.

In sum, embodiments of the technology find use to control drug and/or hormone release in a host without the negative impact of rejection or the use of immunosuppressant drugs. That is, embodiments provide a device and/or system that is implanted into a host to provide and/or control the release of drug and/or hormone without the negative impact of rejection or the use of immunosuppressant drugs.

Subjects

In some embodiments, subjects for treatment include animals, e.g., mammalian species such as humans, and domestic animals such as dogs, cats and the like, subject to a disease and other pathological conditions. A "patient" refers to a subject, preferably mammalian (including human), and preferably a large mammal.

Embodiments of the technology relate to the treatment of a biological organism in need of treatment with a biological material and/or a bioactive agent encapsulated in a membrane pouch or a hydrogel as described herein. The technology is not limited in the subject or biological material (or bioactive agent) provided to the subject in an embodiment of the technology described herein.

In some embodiments, the subject is a female. In some embodiments, the subject is a juvenile or child and in some embodiments the subject is an adult (e.g., a subject who has passed the point of puberty). In some embodiments, the subject has abnormally low levels of a sex hormone. In some embodiments, the subject has been treated for a cancer (e.g., a cancer of the reproductive system and/or a cancer of another system or tissue whereupon cancer treatment has caused a decrease in the amount of sex hormones in the subject). In some embodiments, the subject is an individual who has low levels of a sex hormone due to natural ageing processes, e.g., in some embodiments, the subject is a female who is experiencing the symptoms of menopause (e.g., a female in menopause or who has had menopause).

Methods of Treatment

The administration of the immunoisolation device described herein may be for a "prophylactic" or "therapeutic" purpose. The administration is said to be for a "therapeutic" purpose if the biological material administered is physiologically significant to provide a therapy for an actual manifestation of the disease, disorder, condition, or to alleviate a symptom that is present in the subject. In some embodiments, when provided therapeutically, the immunoisolation device is preferably provided at (or shortly after) the identification of a symptom, e.g., of a disease, disorder, or condition. In some embodiments, the therapeutic administration attenuates the severity of such disease, disorder, or condition or to reverse the progress of such disease, disorder, or condition, or to alleviate a symptom (that, in some embodiments, is present in a normal patient). The administration is said to be for a "prophylactic" purpose if the biological material administered is physiologically significant to provide a therapy for a potential disease, disorder, or condition, or to provide relief from a potential symptom. In some embodiments, when provided prophylactically, the immunoisolation device is provided in advance of any symptom thereof. The prophylactic administration attenuates the advance of the severity of such disease, disorder, or condition, or attenuates the severity of a symptom (that, in some embodiments, is present in a normal patient).

Providing a therapy or "treating" refers to any indicia of success in the treatment or amelioration of an injury, pathology, or condition, including any objective or subjective parameter such as abatement, remission, diminishing of symptoms or making the injury, pathology, or condition more tolerable to the patient, slowing in the rate of degeneration or decline, making the final point of degeneration less debilitating, or improving a patient's physical or mental well-being. The treatment or amelioration of symptoms can be based on objective or subjective parameters, including the results of a physical examination, neuropsychiatric exams, and/or a psychiatric evaluation. For example, the methods of the invention successfully treat a patient's endocrine deficiency by normalizing the subject's sex hormone levels, which is evident upon administration of an assay for measuring the subject's sex hormone levels.

In some embodiments, the immunoisolation device is used as a hormone-producing system, which can be used to treat, e.g., an endocrine disorder. For example, a pancreatic disorder can be treated by implanting an immunoisolation device comprising one or more types of pancreatic tissue or cells such as alpha cells, beta cells, centroacinar cells, delta cells, epsilon cells, pancreatic basophilic cells, PP cells (F cells), acini, or Islets of Langerhans into a patient. Similarly, a thyroid disorder can be treated by implanting an immunoisolation device comprising one or more types of thyroid tissue such as thyroid epithelial cells (follicular cells), parafollicular cells, or follicles into a patient.

A variety of administration routes for the immunoisolation device are available. The particular mode selected depends upon the particular biological material selected, whether the administration is for prevention, diagnosis, or treatment of disease, the severity of the medical disorder being treated and the desired therapeutic efficacy. The duration of prophylactic and therapeutic treatment also varies depending on the particular disease or condition being treated. Some diseases lend themselves to acute treatment whereas others require long-term therapy.

Treatment using the immunoisolation device comprising a biological material involves the transplantation of immunoisolation device into the body cavity of the subject. This may be performed by creating a surgical opening in the body cavity and introducing the immunoisolation device into the body cavity through the opening. This may be accomplished through plausibly simple techniques, such as placing the immunoisolation device through the opening and introducing them into the body cavity. Other techniques known in the art, such as hypodermic injections, may also be used.

Once inside the body cavity, some embodiments provide that the immunoisolation device may move in the body cavity.

Generally, the immunoisolation device is surgically implanted, for example laparoscopically, into an appropriate location in the body, and may be placed therein or affixed to the surrounding tissue.

In an embodiment for the treatment of an endocrine disorder or deficiency, a method of treatment comprises implantation of an immunoisolation device comprising hormone-producing cells that provides a sustained release of hormone. The device does not exhibit significant degradation during the sustained-release period. The term "sustained release," as used herein, refers to the continual release of the bioactive agent from the biological material during instances when the release should take place. For instance, if the biological material is an ovarian cell and the biological agent is estrogen and/or progesterone, the ovarian cells should, after transplantation, release the estrogen and/or progesterone into the host any time the ovarian cells recognize that the estrogen and/or progesterone level of the host has reached a certain point. After the estrogen and/or progesterone level in the host has been maintained, the ovarian cells temporarily cease or decrease secreting additional estrogen and/or progesterone. However, when the estrogen and/or progesterone levels in the host again reach a point where estrogen and/or progesterone is needed, the temporarily-dormant ovarian cells again secrete estrogen and/or progesterone. This type of continual release is an example of sustained release.

In some embodiments, the sustained-release period is 1 to 7 days; 7 to 14 days; 14 to 21 days; and, in some embodiments, 21 to 30 or more days (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more days). In some embodiments, the sustained-release period is more than 30 days, e.g., 31 to 60 days, 60 to 90 days, or more. In some embodiments, the sustained-release period is 1, 2, 3, 4, 5, 6, 7, 8, 9, 10, 11, 12, 13, 14, 15, 16, 17, 18, 19, 20, 21, 22, 23, 24, 25, or 26 or more weeks; in some embodiments, the sustained-release period is 1, 2, 3, 4, 5, 6, 7, 8, 9, 10, 11, or 12 or more months.

The longer the device provides a sustained release of the bioactive agent, the longer the patient will be functioning on the transplanted cells in the device alone without needing additional treatment.

The technology finds use in the treatment of a human, e.g., by transplant in a human host in need of transplant of cells. For example, some embodiments provide that the device is provided by subcutaneous implantation in the host, e.g., in the arm, abdomen, or upper back of the host. Such placement is minimally invasive and provides for access to the device for retrieval of the device and/or cells and provides for reloading the device with fresh cells, if needed.

Additional aspects of the technology provided herein are described throughout this disclosure. Although the disclosure herein refers to certain illustrated embodiments, it is to be understood that these embodiments are presented by way of example and not by way of limitation.

EXAMPLES

The technology relates to an encapsulating device, e.g., to provide immunoisolation of a therapeutic (e.g., a drug, a tissue, a cell, etc.). Data collected from the experiments indicate that isogeneic ovarian tissue encapsulated in an immunoisolating device and implanted in an ovariectomized mouse restores ovarian endocrine function. The implanted ovarian tissue continued to function as confirmed by histological analysis of the implants and measured hormone levels in the serum. In conclusion, ovarian tissue encapsulated in embodiments of the devices described herein responded to the physiological signals and secreted sex hormones and the levels of secreted hormones improved the hormonal profile to normal (e.g., pre-ovariectomy) levels.

Example 1—Encapsulating Devices Comprising Two PEG Layers

In some embodiments the encapsulating device is a two-layer encapsulating device that comprises an "outer shell" and an "inner core". In particular embodiments, the outer shell of the encapsulating device is prepared with a non-degradable PEG (e.g., a PEG crosslinked by exposure to ultraviolet radiation) and the inner core is prepared with a degradable PEG (e.g., a degradable PEG hydrogel, e.g., crosslinked with a protease degradable linker peptide). The non-degradable outer shell of this design provides immune isolation of a therapeutic placed within the inner core and, in embodiments in which the therapeutic comprises cells or tissues, the degradable inner core allows the implanted cell or tissue to expand as it grows. During the development of embodiments of the technology, embodiments of the two-layer encapsulating device were produced and experiments were conducted to characterize the two-layer encapsulating device in vitro. In particular, data were collected describing the degree of swelling, pore size, diffusion rate, and permeability of embodiments of the two-layer encapsulating device. Further experiments were conducted to collect data describing the biocompatibility of the two-layer encapsulating device in an isogenic model and to evaluate the immunoisolation of a therapeutic by the two-layer encapsulating device.

Accordingly, during the development of embodiments of the technology described herein, experiments were conducted to produce embodiments of the two-layer encapsulating device described herein. In particular, in some embodiments the two-layer encapsulating device comprised two poly(ethylene glycol) (PEG) hydrogels, e.g., a first PEG hydrogel that provided a degradable inner core and a second PEG hydrogel that provided a non-degradable outer shell. Therapeutics (e.g., tissue, e.g., ovarian tissue) were implanted in the inner core of embodiments of the two-layer PEG encapsulating devices and the immunoisolation provided by the devices for the therapeutics was tested.

1.1 Materials and Methods

Poly(ethylene) glycol (PEG)

PEG was obtained as a powder with greater than 90% purity (JenKem Technology USA, Plano, TX) and used to prepare sterile solutions with varying PEG concentrations as described below.

Degradable Hydrogel Preparation

Proteolytically degradable PEG vinyl sulfone hydrogels ("D-PEG-VS") were prepared with 8-arm PEG-VS (tripentaerythritol core; Mw=40 kDa) obtained from JenKem, catalog number "8ARM(TP)-VS". The 8-arm PEG-VS was dissolved at 5% to 10% (w/v) final concentration in an isotonic HEPES buffer (0.1 M HEPES, 0.1 M NaCl, pH 7.4) to prepare a degradable PEG vinyl sulfone hydrogel precursor solution. The degradable PEG vinyl sulfone hydrogel precursor solution was then mixed with a plasmin sensitive cross-linker having 3 reactive thiols at a 1:1 molar ratio of -SH and -VS groups. The plasmin sensitive cross-linker was a custom synthesis (Genscript, Piscataway, NJ) and has the amino acid sequence:

```
                              (SEQ ID NO: 1)
Ac-GCYK↓NSGCYK↓NSCG
```

In the amino acid sequence of the plasmin-sensitive cross-linking peptide, the N-terminal acetyl group is added to remove the electrical charge on this terminal. The arrows indicate the protease cleavage sites. That is, the peptide has an amino acid sequence according to:

```
                              (SEQ ID NO: 2)
GCYKNSGCYKNSCG
```

with an N-terminal acetyl group and is cleaved by a protease (e.g., plasmin) between lysine and asparagine in the sequence, e.g., after the lysine at position 4 and/or after the lysine at position 10.

Furthermore, during the development of embodiments of the technology, a peptide was designed that has the amino acid sequence:

```
                              (SEQ ID NO: 3)
GCRDVPMS↓MRGGDRCGYK↓NSCG
```

This peptide is sensitive to both plasmin and MMP proteases. In the amino acid sequence of the peptide that is both plasmin-sensitive and MMP-sensitive, the arrows indicate the protease cleavage sites. That is, embodiments comprise use of a peptide that has an amino acid sequence according to:

```
                              (SEQ ID NO: 4)
GCRDVPMSMRGGDRCGYKNSCG
```

that is cleaved by a protease (e.g., MMP) between serine and methionine in the sequence at positions 8 and 9 and/or that is cleaved by a protease (e.g., plasmin) between the lysine and asparagine in the sequence at positions 18 and 19.

Mixing the PEG vinyl sulfone hydrogel precursor solution and the plasmin sensitive cross-linker initiated a Michael-Type addition reaction that was allowed to proceed for at least 5 minutes to cross-link the PEG vinyl sulfone hydrogel and produce the degradable PEG vinyl sulfone hydrogel.

Non-Degradable Hydrogel Preparation

Non-degradable PEG vinyl sulfone hydrogels ("ND-PEG-VS") were prepared with 4-arm PEG-VS (pentaerythritol core; Mw=20 kDa) obtained from JenKem, catalog number "A7025-1" or "4ARM-VS". The 4-arm PEG-VS was dissolved at 5% to 10% (w/v) final concentration in sterile Dulbecco's phosphate buffered saline (D-PBS) (pH 7.4) containing 0.4 mg/100 μl of a photoinitiator (e.g., such as an alpha hydroxy ketone, e.g., 2-hydroxy-4'-(2-hydroxyethoxy)-2-methylpropiophenone sold as IRGACURE 2959 (BASF, Material No. 55047962) (see, e.g., Elisseeff et al. (2005) *Biomaterials* 26(11): 1211-18, incorporated herein by reference)) and 0.1% (v/v) N-vinyl-2-pyrrilidone (PVP) (Sigma-Aldrich, St. Louis, USA) to prepare a non-degradable PEG vinyl sulfone hydrogel precursor solution. PVP has been shown to enhance gelation without impacting cytocompatibility (see, e.g., Lin et al (2014) *Acta Biomater* 10(1): 104-14, incorporated herein by reference).

The non-degradable PEG vinyl sulfone hydrogel precursor solutions were prepared at final concentrations of 5% to 10% (w/v), which is equivalent to 2.5-30 mg/100 μl of PEG-VS. The non-degradable PEG vinyl sulfone hydrogel precursor solutions were exposed to ultraviolet light at a constant intensity (1090 μW/cm 2 at a distance of 4 cm) for varying radiation times (e.g., from 3-10 minutes) to prepare the non-degradable PEG vinyl sulfone hydrogel.

Dual Hydrogel Preparation

A degradable PEG vinyl sulfone hydrogel ("D-PEG-VS") was prepared as described above to provide the "inner core" of a dual PEG hydrogel preparation. After the gelation of the inner (degradable) core was complete (approximately 7-10 minutes, depending on solid concentration), the crosslinked inner core was transferred to the center of a 10-μl bead of the non-degradable PEG vinyl sulfone hydrogel precursor solution as described above and exposed to ultraviolet light at a constant intensity (1090 $\mu W/cm^2$ at a distance of 4 cm) for varying radiation times (from approximately 3-10 minutes) to provide the "outer shell" around the "inner core".

Swelling Ratio Measurements

Compositions of ND-PEG-VS and D-PEG-VS (n=5) were manufactured and soaked in D-PBS (pH=7.4) for 24 hours. The mass swelling ratio ($Q_m$) was determined as the ratio of the wet mass and dry mass ($Q_m=m_s/m_d$), wherein the wet mass ($m_s$) was the mass of the hydrogels after soaking in D-PBS for 24 hours and the dry mass ($m_d$) was the theoretical polymer mass.

Rheology

Storage modulus (G') of the two components of the dual hydrogel (ND-PEG-VS and D-PEG-VS) was measured at 37° C. using a DHR-2 Rheometer (TA Instruments, New Castle, DE) and a parallel plate geometry (diameter of 20 mm, gap of 1000 μm). The limits of viscoelasticity were determined via a strain sweep experiment with strain range from 0.01% to 0.1% and angular frequency from 0.1 to 100 rad/s. Storage moduli were found at a constant strain of 0.1% and angular frequency from 0.1 to 10 rad/s. The gels were prepared as described and soaked in D-PBS (pH=7.4) for 24 hours prior to the experiment.

Diffusion

Compositions of ND-PEG-VS (e.g., at 5% and 10% (w/v)) were prepared and soaked in a range of dextran solutions (1 mg/ml) prepared using dextrans of varying sizes (5, 70, 150 kDa) for 24 hours at ambient room temperature. After soaking, gels were washed in D-PBS to remove excess dextran solution on the surface of gels. To quantify the release of the dextrans of the various sizes from the hydrogels, hydrogels that had absorbed dextran for 24 hours were transferred to fresh D-PBS at ambient room temperature after 6, 12, 30, 60, 90, and 120 minutes to maintain near sink conditions and fluorescence was quantified using a Fluoroskan Ascent FL (Thermo Electron Corporation, Finland) spectrophotometer. Relative fluorescence values were correlated to concentration (ng/ml) for the respective dextran solutions. These values were then compared to controls, where loaded gels from dextran solutions were soaked in D-PBS for 24 hours at ambient room temperature.

Ovariectomies in Recipient Mice

Ovariectomies were performed on adult female mice (C57Bl/6JXCBA/Ca and C57Bl/6J) aged 12-16 weeks to induce infertility. The UCUCA guidelines for survival surgery in rodents and the UCUCA Policy on Analgesic Use in Animals Undergoing Surgery were followed for all the procedures. The females were anesthetized by isoflurane. Preemptive analgesics were administered before the first cut was made. Using aseptic techniques and procedures, a midline incision was made in the abdominal wall. The intraperitoneal space was exposed with an abdomen retractor. The ovaries were removed and the remaining reproductive tract was gently reinserted into the body cavity. The muscle layer and the skin of the mouse are then closed with absorbable sutures in two separate layers. The animal was then placed in a clean warmed cage for recovery. Following recovery, the animal was housed in the animal facility.

Collection of Donor Ovaries

Ovaries were collected from 6-8 days old F1 hybrid (C57Bl/6JXCBA/Ca) and Balb/c female pup mice, which have a large number of primordial follicles, and transferred to maintenance media. The ovaries were cut into pieces and kept in the incubator until they were encapsulated for transplantation.

Ovary Encapsulation in D-PEG-VS, ND-PEG-VS and Dual PEG Hydrogels

The encapsulation of the ovarian tissue was performed in a sterile biohazard cabinet on a heating stage to minimize ambient damage to the tissue. To prepare PEG-based implants, ovarian pieces were transferred from the maintenance media in the incubator and were laid on a hydrophobic slide using an insulin (27G) needle. Each ovarian piece was about 1 to 1.5 mm 3 in volume. Droplets (5 μl) of the PEG precursor were pipetted on the same glass slide and ovarian pieces were transferred into a droplet of degradable PEG vinyl sulfone hydrogel precursor solution. To prepare D-PEG-VS, another 5 μl of a dissolved peptide crosslinker were added to the droplet of PEG-VS and mixed. The slide was then covered with a top slide and allowed to form gels for 5 minutes. After the gelation was complete, the hydrogels were ready to be transplanted.

To prepare non-degradable PEG vinyl sulfone hydrogels with ovarian tissue, droplets (10 μl) of PEG vinyl sulfone precursor solutions with the initiator and PVP were pipetted on a hydrophobic glass slide. The pieces of ovarian tissue were placed on the glass and transferred by a needle into the droplets. The PEG-VS precursor solutions with the tissue were exposed to ultraviolet light at a constant intensity (1090 μW/cm 2 at a distance of 4 cm) for varying radiation times (e.g., from 3 to 10 minutes) to prepare the non-degradable PEG vinyl sulfone hydrogel.

For encapsulation of ovarian tissue pieces in dual PEG hydrogel, ovarian pieces were transferred into a droplet of degradable PEG vinyl sulfone hydrogel precursor solution and allowed to gel as described above, then the gelled degradable PEG vinyl sulfone hydrogel was encapsulated in a non-degradable PEG vinyl sulfone hydrogel as described above for the preparation of dual hydrogels.

Subcutaneous Transplantation

Ovarian constructs were implanted subcutaneously in the back of mice. A small incision was made on the skin of the anesthetized mice and the construct (D-PEG-VS, ND-PEG-VS, and dual PEG) containing the ovaries was placed under the skin. The skin was then closed using 5/0 absorbable sutures. The mice were then placed in a clean warmed cage for recovery and monitored post-operatively for a minimum of 7-10 days. Mice receive analgesics for at least 24 hours after surgery or as needed. After transplantation, the mice were euthanized at different time points (7, 26, 60, and 90 days).

Blood Collection for Hormone Analysis

Lateral tail vein blood was collected weekly, 1% of the total body weight in a 53/4" glass Pasteur pipette. The mouse received preemptive analgesia and was restrained in a mouse trap to allow easy access to the tail. The tail was cleaned with an alcohol swab. Using a sharp scalpel, a cut at the distal tail was made. At the time of sacrifice, blood was collected via cardiac puncture, maintained at 4° C. overnight, then centrifuged for 10 minutes and the serum collected and stored at −20° C. Samples were diluted to one-fifth or one-tenth concentrations for measuring follicle stimulating hormone (FSH) and estradiol (E2).

Histological Analysis

Hydrogels (D-PEG-VS, ND-PEG-VS, and dual-PEG) were fixed in Bouin's fixative at 4° C. overnight and transferred to 70% ethanol at 4° C. until they were processed. Samples were embedded in paraffin, serially sectioned at 5-μm thickness, and stained with hematoxylin and eosin. Primordial follicles were characterized by one layer of flattened granulosa cells around the oocyte, primary follicles were characterized by one layer of cuboidal granulosa cells, secondary follicles were characterized by two or more layers of granulosa cells, and antral follicles were characterized by the presence of an antral cavity.

1.2 Results

Histology

PEG hydrogel encapsulation device comprising ovarian tissue was implanted in the back of ovariectomized mouse for 30, 60, and 90 days. Histological data collected indicated that growing ovarian follicles were present at all the developmental stages. Further, histological images showed multiple growing follicles and the ovarian tissue was surrounded by the hydrogel.

D-PEG-VS Functionality—Cyclicity and Hormone Levels

In mice implanted with D-PEG-VS for a period of up to 60 days, decreased FSH levels were observed compared to ovariectomized levels. Following implantation of 10% D-PEG-VS for a period of 60 days, the FSH levels decreased from 70 to 35 ng/ml, which indicated functional ovarian tissue.

10% D-PEG-VS Functionality—Histological Analysis and Follicular Proportions

After 7 days of implantation, follicular development up to the secondary stage was observed: 43% of follicles were primordial follicles; 40% of follicles were primary follicles; 17% of follicles were secondary follicles. After 30 days of implantation of 10% D-PEG-VS, follicular development up to the antral stage was observed. Of the total follicular pool, 13% of follicles were primordial follicles, 38% of follicles were primary follicles; 38% of follicles were secondary follicles: and 10% of follicles were antral follicles.

5% D-PEG-VS Functionality—Cyclicity and Hormone Levels

After implantation of 5% D-PEG-VS for a period of 30 days, the success rate in terms of restoration of estrus cycles was 100% at the end of the time period (n=3). Mice vaginal cytology was used for correlation of ovarian endocrine functionality. Success was characterized by observing mice that had a normal estrus cycle post-implantation of 5% D-PEG-VS hydrogels.

5% D-PEG-VS Functionality—Histological Analysis and Follicular Proportions

After 30 days of implantation, follicular development up to the antral stage was observed: 12% of follicles were primordial follicles; 62% of follicles were primary follicles; 23% of follicles were secondary follicles; and 4% of follicles were antral follicles.

ND-PEG-VS Functionality

After implantation of the ND-PEG-VS construct (n=8), 65% of mice resumed cyclicity after 1 week, 100% were cycling after 4 weeks, yet 7 weeks post-transplantation only 50% of the mice retained normal estrous cycle. This level of success correlated with FSH levels, which remained elevated at a level of 55 ng/ml at 60 days post transplantation. Following histological analysis, the encapsulated ovarian tissue was necrotic after 7 and 30 days of implantation. In mice that were implanted with the encapsulated tissue for 7 days, 80% exhibited decreased FSH levels compared to ovariectomized levels. However, hormone levels would not be expected to change after a 7-day implantation of encapsulated ovarian tissue in the hydrogel. Importantly, failure was not due to rejection from the host in this syngeneic model because the ovarian tissue was completely encapsulated. Without being bound by theory, it is contemplated that the rigidity and stability (e.g., being non-degradable) of ND-PEG-VS hinders the follicles from growing, expanding, and maintaining functionality.

Dual PEG Functionality

Of the mice implanted with ovarian tissue encapsulated within a dual PEG construct in the syngeneic model (n=3), two of the mice cycled post-transplantation (a success rate of 67%). Of the mice implanted with ovarian tissue encapsulated within dual PEG in the allogeneic model (n=3), one of the mice cycled post transplantation (a success rate of 33%). As described herein, the dual PEG construct comprises ovarian tissue completely encapsulated in a D-PEG "inner core" and the D-PEG "inner core" is surrounded by a ND-PEG "outer shell".

Physical Characterization

The technology contemplates combining D-PEG and ND-PEG to provide an environment for encapsulated follicles to grow and remain viable and protect the encapsulated follicles from an immunological response (e.g., in an allogeneic host). Accordingly, without being bound by theory, it is contemplated that the D-PEG is less stiff than ND-PEG; in particular, it is contemplated that the more elastic D-PEG hydrogel does not apply as much compression against expanding follicles as does the ND-PEG and, in some embodiments, that the D-PEG hydrogel is degraded by the cells as the cells grow in the core of the device.

Swelling ratio provides a convenient measurable value to characterize the stiffness of hydrogels. In particular, hydrogels that swell substantially (e.g., have a high or higher swelling ratio) are softer and have a lower storage modulus and a larger pore size compared to hydrogels that swell less. As described below, the data collected indicated that swelling ratio increased as the PEG concentration decreased, indicating an inverse relationship between PEG concentration and swelling (e.g., a low PEG concentration correlated well with a low storage modulus and high swelling ratio).

During the development of embodiments of the technology described herein, experiments were conducted to measure the swelling ratio of D-PEG and ND-PEG. Swelling ratio is inversely related to stiffness—a higher swelling ratio indicates a less stiff gel having a lower storage modulus. Data were collected during experiments that indicated that D-PEG is less stiff than ND-PEG as indicated by the associated swelling ratios of D-PEG and ND-PEG over a broad range of PEG concentrations tested.

Furthermore, during the development of embodiments of the technology described herein, experiments were conducted to measure the swelling ratios of ND-PEG-VS hydrogels as a function of PEG concentration, amount of photoinitiator, and cross-linking time (see, e.g., FIG. 1). In particular:

1) ND-PEG-VS hydrogels were produced using 0.5% photoinitiator at 2.5 mg PEG/100 μl, 5 mg PEG/100 μl, and 10 mg PEG/100 μl; and with cross-linking times of 1 minute, 3 minutes, and 5 minutes (see, e.g., FIG. 1A);
2) ND-PEG-VS hydrogels were produced using 0.4% photoinitiator at 2.5 mg PEG/100 μl, 5 mg PEG/100 μl, and 10 mg PEG/100 μl; and with cross-linking times of 3 minutes and 5 minutes(see, e.g., FIG. 1B);
3) ND-PEG-VS hydrogels were produced using 0.3% photoinitiator at 2.5 mg PEG/100 μl, 5 mg PEG/100 μl, and 10 mg PEG/100 μl; and with cross-linking times of 3 minutes and 5 minutes (see, e.g., FIG. 1C); and
4) D-PEG-VS hydrogels were produced using 5 mg PEG/100 μl and 10 mg PEG/100 μl; and with cross-linking times of 5 minutes and 10 minutes (see, e.g., FIG. 1D).

The data collected indicated that swelling ratio increased as the PEG concentration decreased.

Furthermore, rheological data were collected during the development of embodiments of the technology (see, e.g., FIG. 2). In particular, the rheological data further indicates that D-PEG is less stiff than ND-PEG. In ND-PEG and D-PEG sample preparations having a PEG concentration of 5% (w/v) and cross-linked for 5 minutes, the storage modulus measured for the ND-PEG preparation was of 3536.69±189.12 Pa and the storage modulus measured for D-PEG was 2495.63±242.01 Pa. Additionally, it was observed that the photoinitiator concentration had a limited effect on the characteristics of the gel; accordingly, 0.4% (w/v) photoinitiator was selected due to ease of manufacturing. With respect to the effect of increasing the ND-PEG concentration, the rheological results supported the observed swelling ratios; in particular, higher PEG concentrations were observed to produce hydrogels having greater storage moduli. Without being bound by theory, it is contemplated that increasing the PEG concentration provides an increased number of reactive sites being available to form free radicals; thus, more cross-bridges form in preparations comprising higher PEG concentrations. For example, an increase in PEG concentration from 5% to 10% w/v (radiated for 5 minutes) results in a significant increase in storage modulus G' from 3536.69±189.12 Pa at 5% PEG to 7704.50±500.78 Pa at 10% PEG.

Figures 3, 3C:
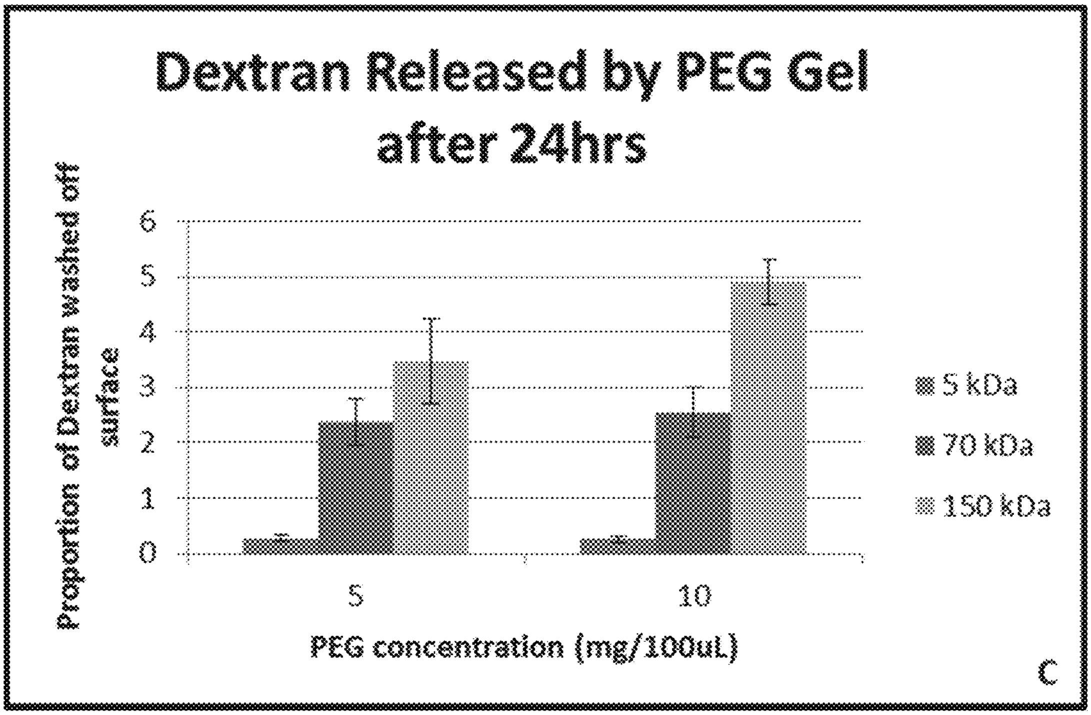
FIG. 3 is a series of plots showing diffusion of varying dextran sizes over time in 5% (FIG. 3A) and 10% (FIG. 3B) ND-PEG-VS.
FIG. 3C is a plot showing the proportion of varying dextran sizes washed off the surface of the PEG hydrogels after a 24 hour soak relative to the dextran released over 24 hours.

During the development of embodiments of the technology provided herein, experiments were conducted to determine the size exclusion barrier of the ND-PEG-VS outer shell (see, e.g., FIG. 3). In particular, experiments measured release of dextrans having different sizes (e.g., 5 kDa, 70 kDa, and 150 kDa) from hydrogels. It was contemplated that the ND-PEG-VS would be permeable to smaller size particles (e.g., having a size similar to nutrients and hormones) and would not be permeable to larger particles (e.g., having a size similar to host immune cells and antibodies). Data collected from the experiments indicated that the 5 kDa particles passed through the ND-PEG-VS hydrogel and passage of the 70 kDa and 150 kDa particles were inhibited by the ND-PEG-VS hydrogel (see, e.g., FIG. 3A and FIG. 3B). In particular, the concentration of released 5 kDa particles increased substantially as a function of time before reaching equilibrium (see, e.g., FIG. 3A and FIG. 3B). In contrast, a small amount of particles ranging from 70 kDa to 150 kDa penetrates the gel initially (e.g., at early time points) and an equilibrium is quickly reached (see, e.g., FIG. 3A and FIG. 3B).

In addition, the data collected indicated that the proportion of particles that are washed off and adsorbed on the surface compared to the particles that penetrate the gel increasing substantially as the size of the particle increases (FIG. 3C). For example, the amount of 150 kDa dextran washed off 5% ND-PEG gels was approximately 350% greater than the amount that was released from the gel over 24 hours. In contrast, the amount of 5 kDa dextran washed off 5% ND-PEG gels was approximately 27% of the amount that was released from the gels over 24 hours. Thus, these results indicate that the hydrogels exclude larger sized particles and are permeable to smaller sized particles. That is, the larger the size of the particle, the more that will be excluded from penetrating the hydrogel.

Example 2—Encapsulating Devices Comprising a Bilaminar Polytetrafluorethylene Membrane During the development of some embodiments of the technology provided herein, experiments were conducted to test the immunoisolation provided by a synthetic membrane. The synthetic membrane is a bilayer comprising an inner semipermeable membrane made of polytetrofluoroethylene (PTFE) that is laminated to an outer membrane covered by a loose polyester mesh (e.g., commercially available as THERACYTE, TheraCyte, Inc., Laguna Hills, CA).

During the development of embodiments of the technology, experiments were conducted to study implantation of isogenic ovarian tissue implants encapsulated in TheraCyte® for a period of 7 days and 30 days. The experiments were performed in an isogeneic mouse model to minimize or eliminate rejection of implanted tissue. It was contemplated that these experiments would be used to identify the best encapsulation material to support ovarian tissue survival and function, which would be then tested in an allogeneic mouse model to study immunoisolation.

Ovarian tissue isolated from 6-8 days old female mice was dissected into 8-10 pieces and physically inserted in a TheraCyte device having a capacity of 4 μl. The device comprising the tissue was implanted in the subcutaneous space. The tissue was explanted after 7 and 30 days and histological sections were examined for follicle counts and population. The ovarian tissue encapsulated in the device preserved healthy morphology during the implanted period, as observed from histological sections of the ovarian tissue. Growing ovarian follicles at all the developmental stages were observed in multiple sections.

Figure 4:
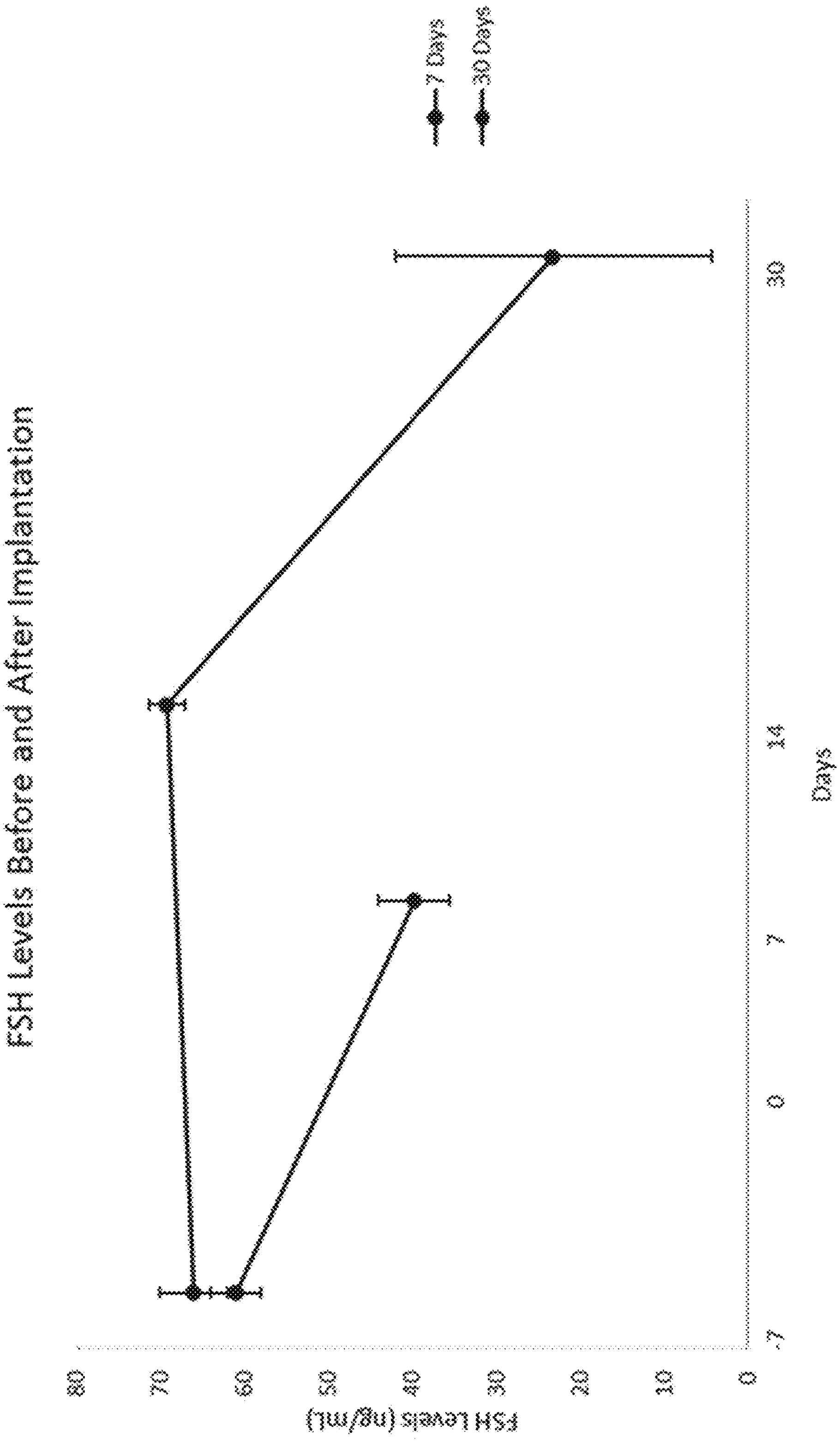
FIG. 4 is a plot showing a decrease in FSH levels in ovariectomized mice after implantation of ovaries encapsulated in TheraCyte® for a period of 7 (lower line) and 30 (top line) days.
Figure 7:
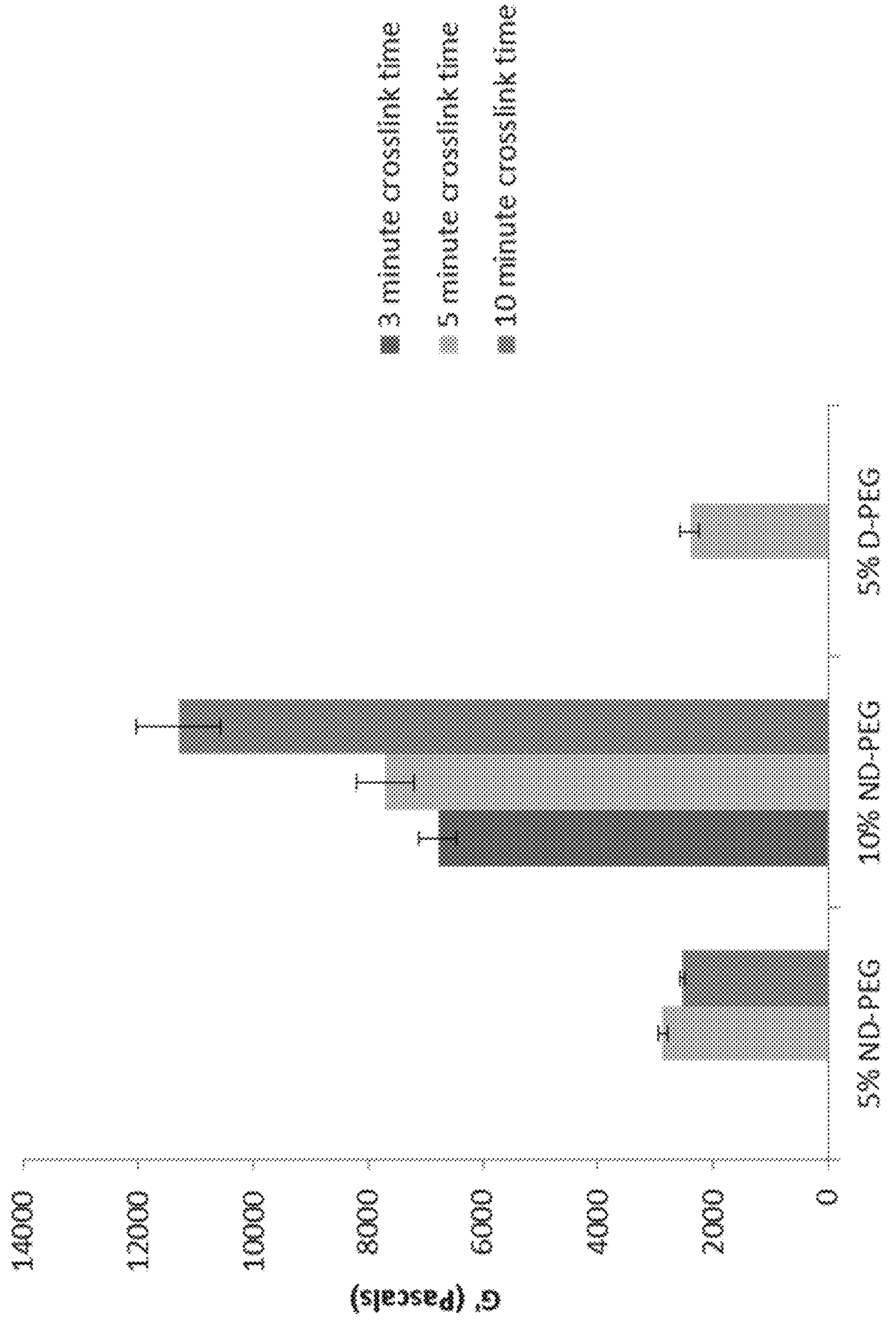
FIG. 7 is a bar plot showing the storage modulus (G') of D-PEG hydrogel and ND-PEG hydrogels formed with 3, 5, and 10 minute crosslinking times.

The data collected indicated a decrease in FSH levels in the ovariectomized mice after implantation of ovaries encapsulated in TheraCyte (FIG. 4 7 days (lower line); 30 days (upper line). This decrease in the circulating FSH levels indicates that the ovarian graft encapsulated in TheraCyte restores the ovarian endocrine function in ovariectomized mice.

Histological images taken 7 days after syngeneic transplantation showed primordial, primary, and secondary follicles. Histological images taken 30 days after syngeneic transplantation showed primordial, secondary, and antral follicles. Initially, the ovarian grafts comprised mainly small immature follicles at the implantation day because the tissue was taken from 6 days old females.

After 7 days of implantation, follicular development up to the secondary stage was observed –73% were primordial follicles, 14% were primary follicles, and 14% were secondary follicles. After 30 days of implantation, follicular development up to the antral stage was observed. Of the total follicular pool, 41% were primordial follicles, 36% were primary follicles, 21% were secondary follicles, and 2% were antral follicles. The distribution of the growing and non-growing follicles resembled the normal physiological state. In sum, the images indicated the presence of healthy live follicles distributed in normal growth states, which indicated successful ovarian graft survival and function.

In addition, decreased FSH levels were observed compared to ovariectomized levels. Following implantation for a period of 30 days, the FSH levels decreased and were statistically significantly lower compared to the ovariectomized levels.

Thus, these experiments indicated that syngeneic implantation of ovarian tissue encapsulated in TheraCyte® restored endocrine function in ovariectomized mice. In particular, follicular development up to the antral stage was observed, and the decrease in FSH compared to the ovariectomized levels indicated the ovarian tissue encapsulated in TheraCyte® functioned to restore endocrine function.

Example 3—Physical and Mechanical Characterization of PEG Hydrogels

During the development of embodiments of the technology described herein, experiments were conducted to characterize the physical and mechanical properties of PEG hydrogels. Data collected during the experiments indicated the conditions and ranges of conditions that provide control of biological aspects of the hydrogels, such as tissue variability, size, source, metabolic rates, and turnover.

The swelling ratio (Qm) of hydrogels provides an indicator of the physical properties of hydrogels (e.g., UV-crosslinked hydrogels), such as stiffness and pore size. In particular, a greater Qm is associated with (e.g., indicates) softer (e.g., less stiff, less rigid) hydrogels and larger pore size.

Figure 5:
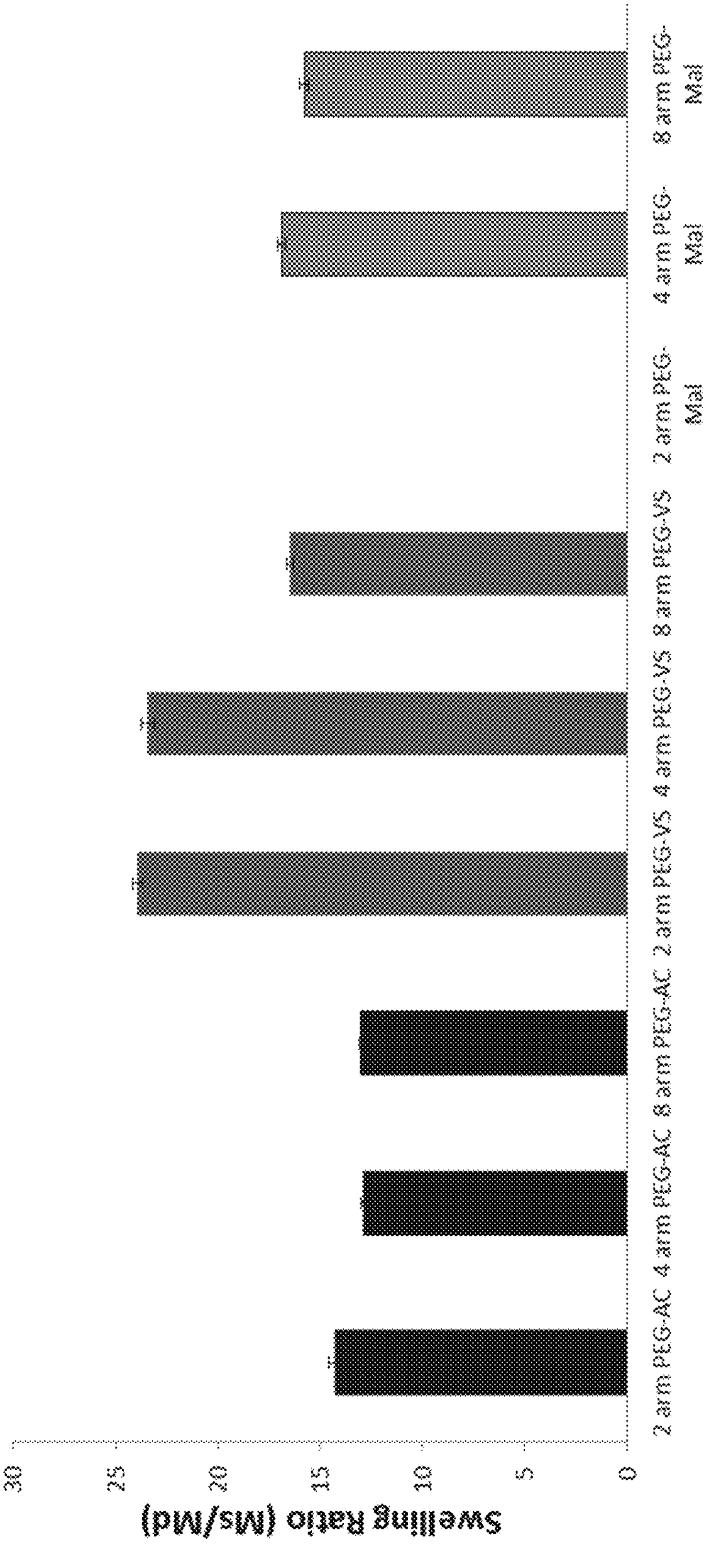
FIG. 5 is a bar plot showing the swelling ratios of PEG-acrylate (PEG-Ac), PEG-vinyl sulfone (PEG-VS), and PEG-maleimide (PEG-Mal) hydrogels.

During the development of embodiments of the technology provided herein, experiments were conducted to test PEG precursors as materials for use in the immunoisolation technology described herein. Data were collected that provided information about the swelling ratio of PEG hydrogels as a function of the reactivity of the active end-group; and the overall functionality of the 2-arm PEG, 4-arm PEG, and 8-arm PEG precursor molecules (FIG. 5). In particular, three different reactive end groups were tested: 1) PEG-acrylate (PEG-Ac); 2) PEG-vinyl sulfone (PEG-VS); and PEG-maleimide (PEG-Mal). While PEG-Ac is susceptible to hydrolytic degradation, both PEG-VS and PEG-Mal are not susceptible to hydrolytic degradation. The experiments indicated that all three reactive groups formed hydrogels with the described UV crosslinking chemistry. Data indicated that the swelling ratio for the three PEG hydrogels were in the same range—the swelling ratio of PEG-VS had the highest value of 35, which was followed by the lower swelling ratios of PEG-Mal and PEG-Ac (FIG. 5).

The crosslinking chemistry of PEG hydrogels can be controlled to provide proteolytically degradable (D-PEG) or proteolytically non-degradable (ND-PEG) hydrogels. For example, in some embodiments a proteolytically degradable PEG hydrogel comprises a crosslinking peptide that is sensitive and degradable by a cell-secreted protease. An exemplary chemistry that finds use in the production of a proteolytically degradable PEG is a Michael-type reaction (e.g., Michael addition) for the nucleophilic addition of a carbanion or another nucleophile to an α,ß-unsaturated carbonyl compound. And, in some embodiments, a non-degradable PEG hydrogel is formed by UV light-induced crosslinking (ND-PEG).

Figure 6:
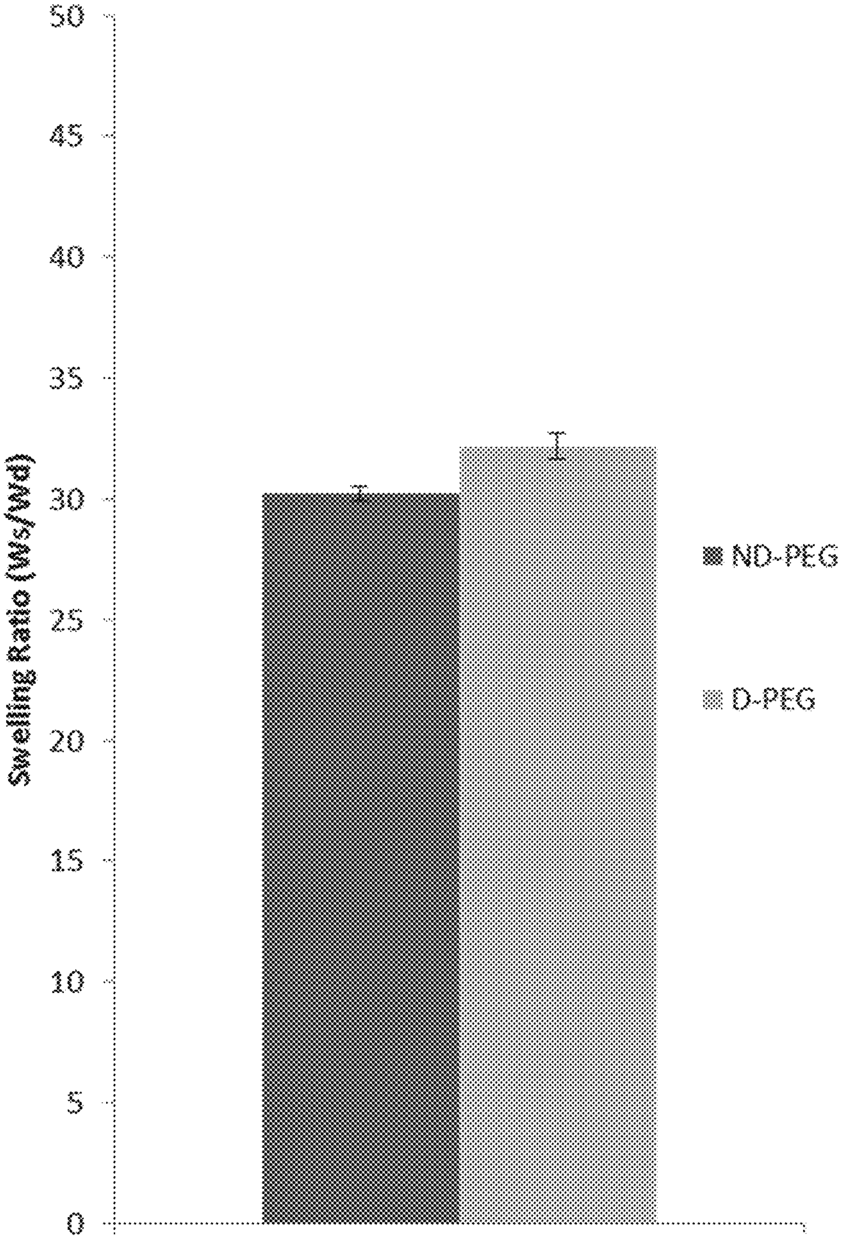
FIG. 6 is a bar plot showing the swelling ratios (Qm) of D-PEG and ND-PEG hydrogels.

In some embodiments, the degradable hydrogel is used to encapsulate a tissue and allow expansion of the tissue; and the non-degradable gel provides a "shell" around the degradable gel comprising the tissue to protect the tissue from immune recognition. Embodiments provide that a degradable hydrogel comprising the tissue is encapsulated in a non-degradable gel. Accordingly, in some embodiments, the physical properties (e.g., swelling and stiffness) of the non-degradable and degradable hydrogels match. Data were collected to characterize the swelling ratio (Qm) of D-PEG and ND-PEG hydrogels, e.g., to provide information about their physical properties (FIG. 6). The data indicated that the ND-PEG (e.g., 5% ND-PEG), that serves as the shell, and the D-PEG (e.g., 5% D-PEG) that provides the core, have matching Qm of approximately 30 (FIG. 6).

Hydrogels are visco-elastic materials. The storage modulus (G') of a gel corresponds with the elastic (solid) properties of a gel; and the loss modulus (G") of a gel corresponds with the viscous (fluid) properties of the gel. During the development of embodiments of the technology provided herein, experiments were conducted to evaluate how the concentration of PEG precursors (5% w/v and 10% w/v), the crosslinking chemistry (UV versus degradable linker), and the crosslinking time (3, 5, and 10 minutes) affect the viscoelastic properties of the gels.

The data collected indicated that the storage moduli (G') of 5% ND-PEG gels was not affected by the crosslinking time and reached 3000 Pa after 5 or 10 minutes of UV irradiation (FIG. 7). 5% ND-PEG did not form after 3 minutes. The data further indicated that the storage moduli of 10% ND-PEG gels was approximately double compared to the storage moduli of 5% ND-PEG hydrogels and increased with the increase in irradiation time (FIG. 7), thus demonstrating tunability of the system. The storage modulus of 5% D-PEG was similar to the 5% ND-PEG (FIG. 7), as was predicted by the Qm values (FIG. 6).

Figure 8:
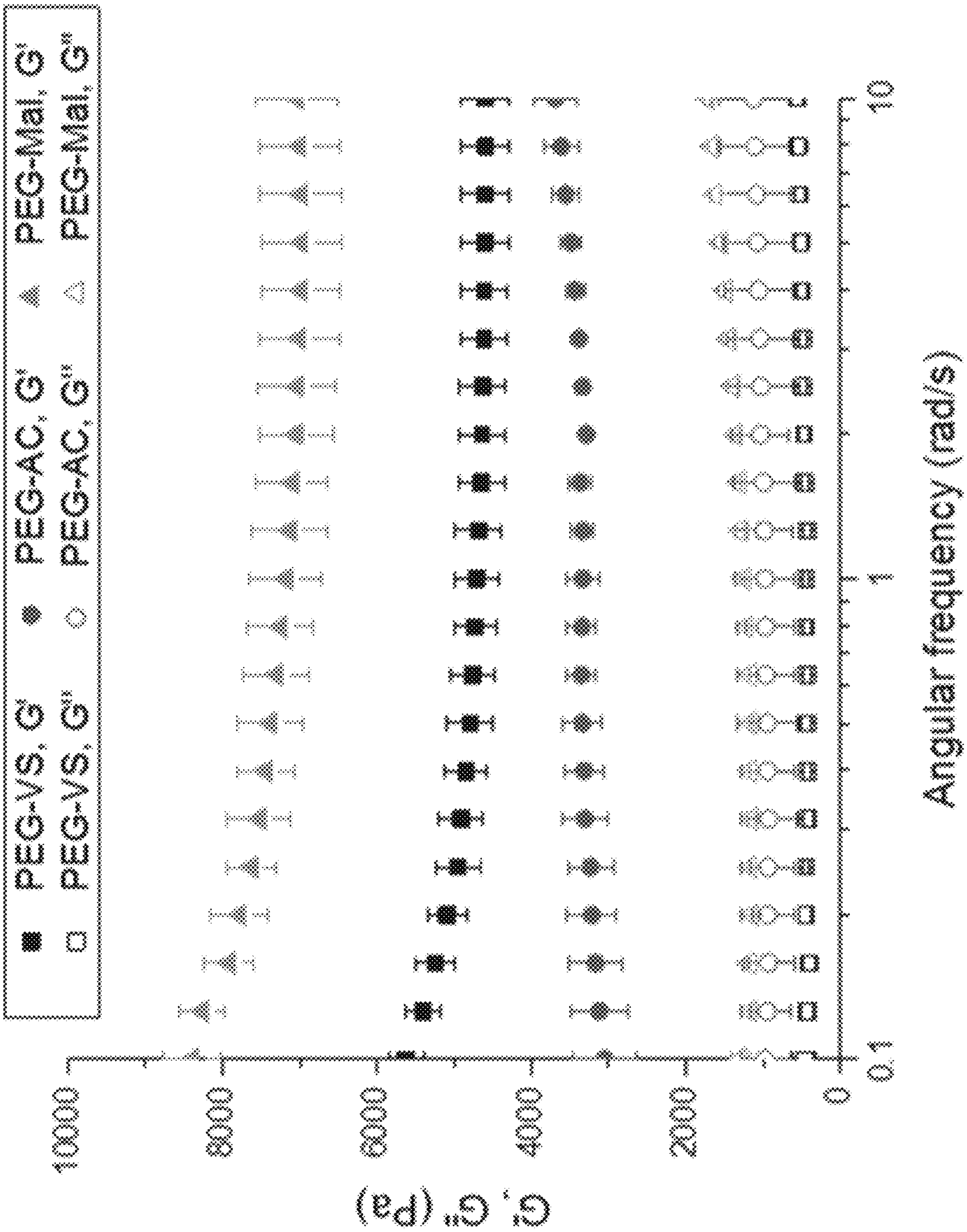
FIG. 8 is a plot showing the storage and loss moduli (G' and G", respectively) measured by rheology for PEG-acrylate (PEG-Ac), PEG-vinyl sulfone (PEG-VS), and PEG-maleimide (PEG-Mal) hydrogels.

During the development of embodiments of the technology provided herein, additional experiments were conducted to test the effect of the end-group chemistry (e.g., acrylate (PEG-Ac), vinyl sulfone (PEG-VS), or maleimide (PEG-Mal)) on the measured storage moduli (G') and loss moduli (G") of 8-arm PEG hydrogels formed with UV irradiation (FIG. 8). Storage and loss moduli were measured using a rheometer. The hydrogels were positioned between the two plates of the rheometer and the moduli of the hydrogels were measured as a function of the increasing frequency (FIG. 8). Data shown are the moduli of the three different hydrogel conditions collected with the same settings. PEG-Ac and PEG-VS were the softer hydrogels reaching G' of about 4000 Pa, while PEG-Mal was two times stiffer. All three hydrogels demonstrated comparable viscous component (e.g., loss moduli) close to 1000 Pa (FIG. 8).

Figure 9:
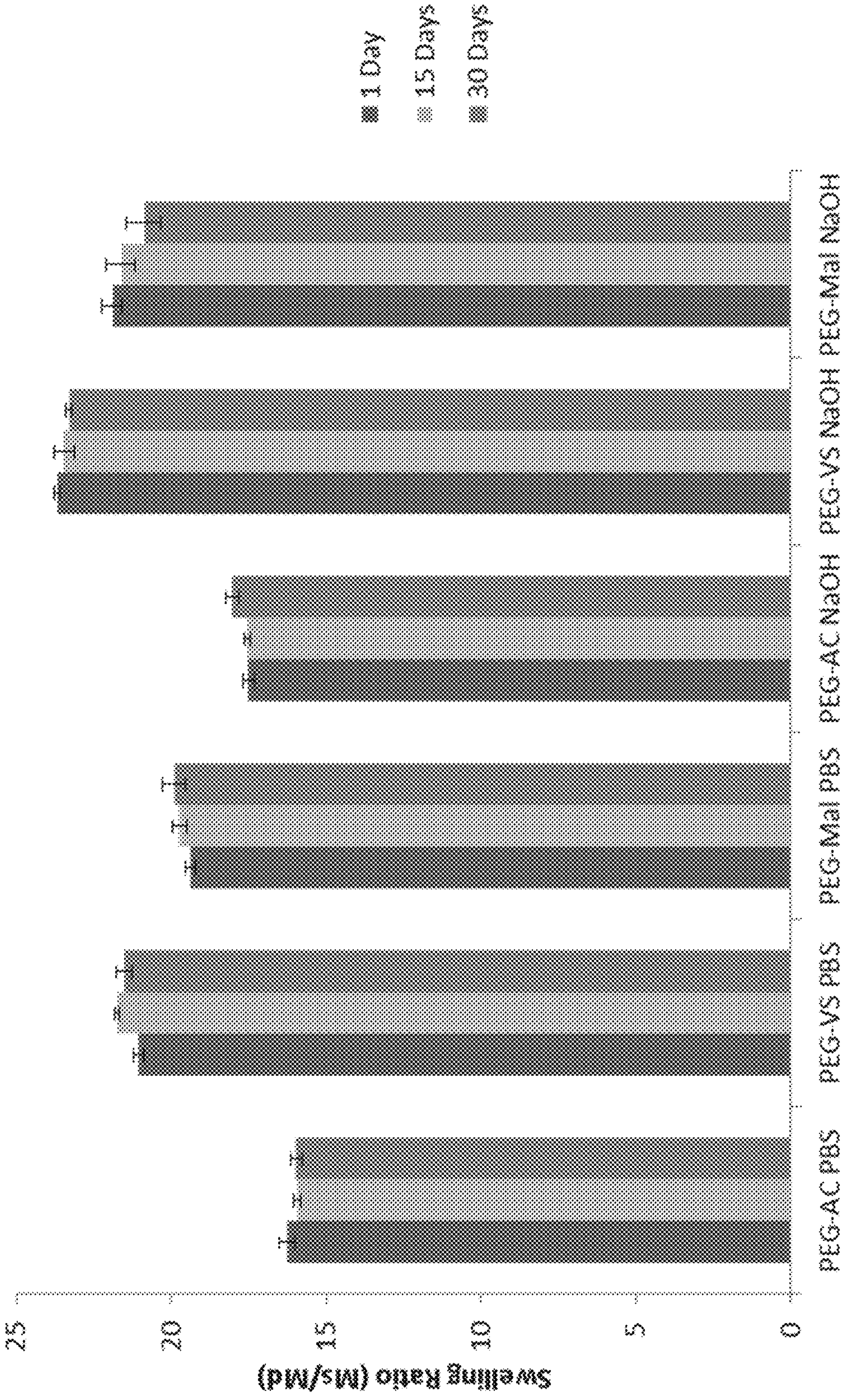
FIG. 9 is a bar plot showing the swelling ratios for PEG-acrylate (PEG-Ac), PEG-vinyl sulfone (PEG-VS), and PEG-maleimide (PEG-Mal) hydrogels incubated in 5 mM buffered and NaOH solutions at 37° C. for 30 days.

During the development of embodiments of the technology provided herein, further experiments were conducted to test the stability of ND-PEG hydrogels crosslinked with UV light. In particular, data were collected to measure the extent of degradation of UV-linked hydrogels in aqueous and basic medium, e.g., in 5 mM buffered and NaOH solutions at 37° C. for 30 days (FIG. 9). The swelling ratio of the hydrogels did not change in any of the conditions indicating that no degradation happened over the course of the 30 days of the experiment. These data indicate that the hydrogels are stable in vivo and thus protect the implanted tissue.

Example 4—In Vivo Testing of Hydrogel Implants

During the development of embodiments of the technology provided herein, experiments were conducted to test the hydrogels in vivo to provide data and information related to the use of hydrogels as immunoisolating devices. In particular, the experiments indicated that the encapsulation, implantation, and function of tissue in vivo are not affected by the hydrogels. That is, the PEG hydrogel supports the survival and function of implanted syngeneic ovarian tissue.

Figure 10:
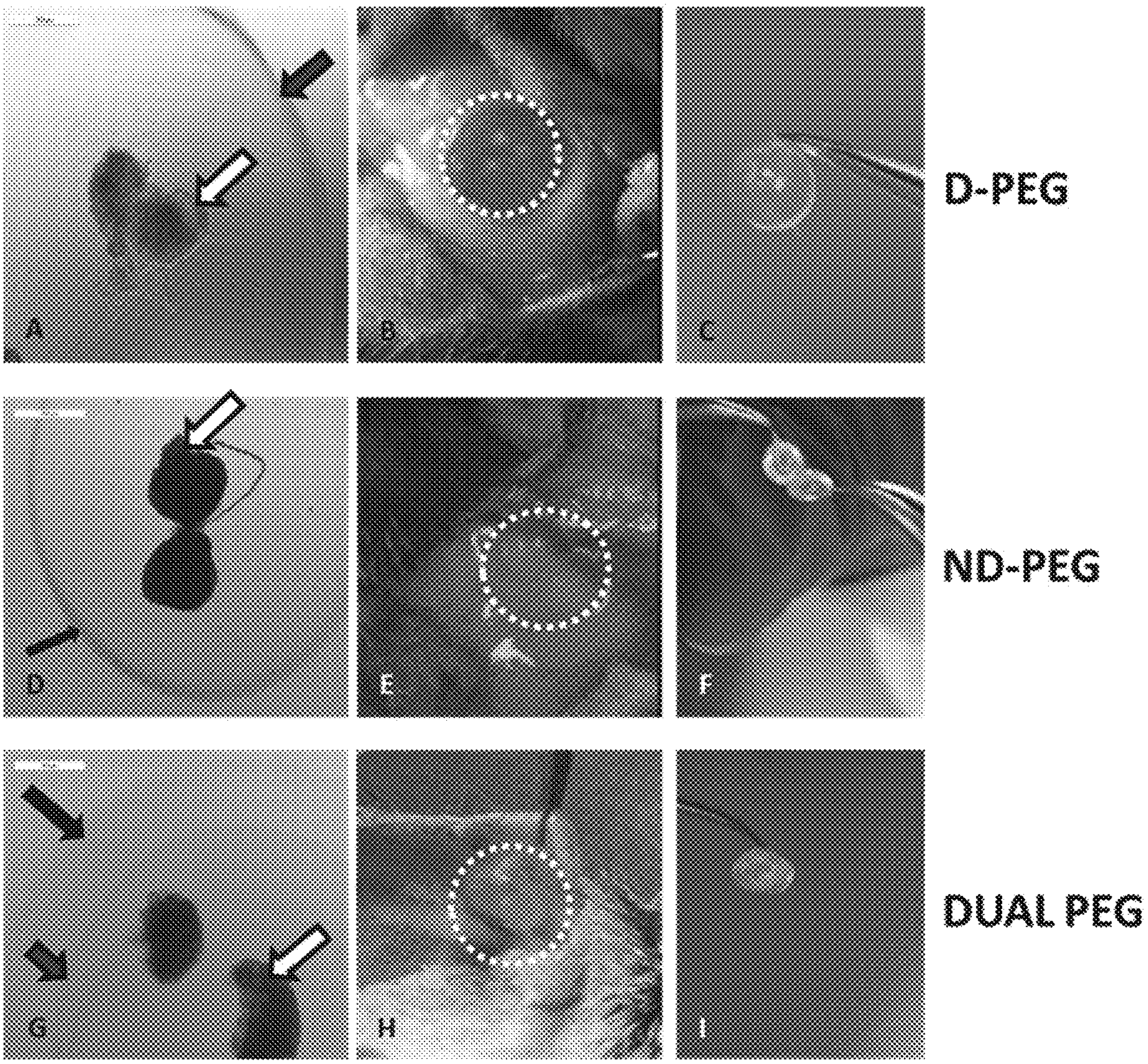
FIG. 10 is a series of micrographs. (10A) ovarian tissue encapsulated in D-PEG; (10B) D-PEG in the subcutaneous space 30 days post implantation; (10C) retrieved D-PEG; (10D) ovarian tissue encapsulated in ND-PEG; (10E) ND-PEG at the time of sacrifice; (10F) retrieved D-PEG; (10G) ovarian tissue encapsulated in Dual-PEG; (10H) dual-PEG at the time of sacrifice; (10I) retrieved dual-PEG after removal. Dotted circle indicates the localization of the hydrogel implanted in the mice. White arrows indicate encapsulated ovarian tissue. Gray arrows indicate the border of D-PEG and black arrows indicate the border of ND-PEG.

During the experiments, images were acquired through a microscope and data were collected to evaluate PEG hydrogels before and after implantation in a subject. FIGS. 10A, 10B, and 10C show tissue implanted in D-PEG. FIGS. 10D, 10E, and 10F show tissue implanted in ND-PEG. FIGS. 10G, 10H, and 10I show tissue implanted in the dual-layer ("Dual-PEG" comprising a ND-PEG outer layer "shell" and D-PEG inner layer "core").

After implantation, the ovarian tissue remained encapsulated in D-PEG (A) and the ovarian tissue encapsulated in D-PEG was observed in the subcutaneous space 30 days post implantation (B). At the end of the experiment, the D-PEG comprising the tissue was retrieved (C).

After implantation, the ovarian tissue remained encapsulated in ND-PEG (D) and remained encapsulated in ND-PEG at the time of sacrifice (E). At the end of the experiment, the ND-PEG comprising the tissue was retrieved (F).

After implantation, the ovarian tissue remained encapsulated in Dual-PEG (G) and remained encapsulated in Dual-PEG at the time of sacrifice (H). At the end of the experiment, the Dual-PEG comprising the tissue was retrieved (I).

In FIGS. 10B, 10E, and 10H, the dotted circle indicates the localization of the hydrogel on the mice. White arrows in FIGS. 10A, 10D, and 10G indicate encapsulated ovarian tissue. Gray arrows in FIGS. 10A and 10G indicate the border of D-PEG and black arrows in FIGS. 10D and 10G indicate the border of ND-PEG. Magnification is 5× in FIGS. 10A, 10D, and 10G. All PEG hydrogels were transparent after preparation, the tissue remained encapsulated during the implanted period, and minimal fibrous capsule formation was visible when the hydrogels were retrieved.

Figure 11:
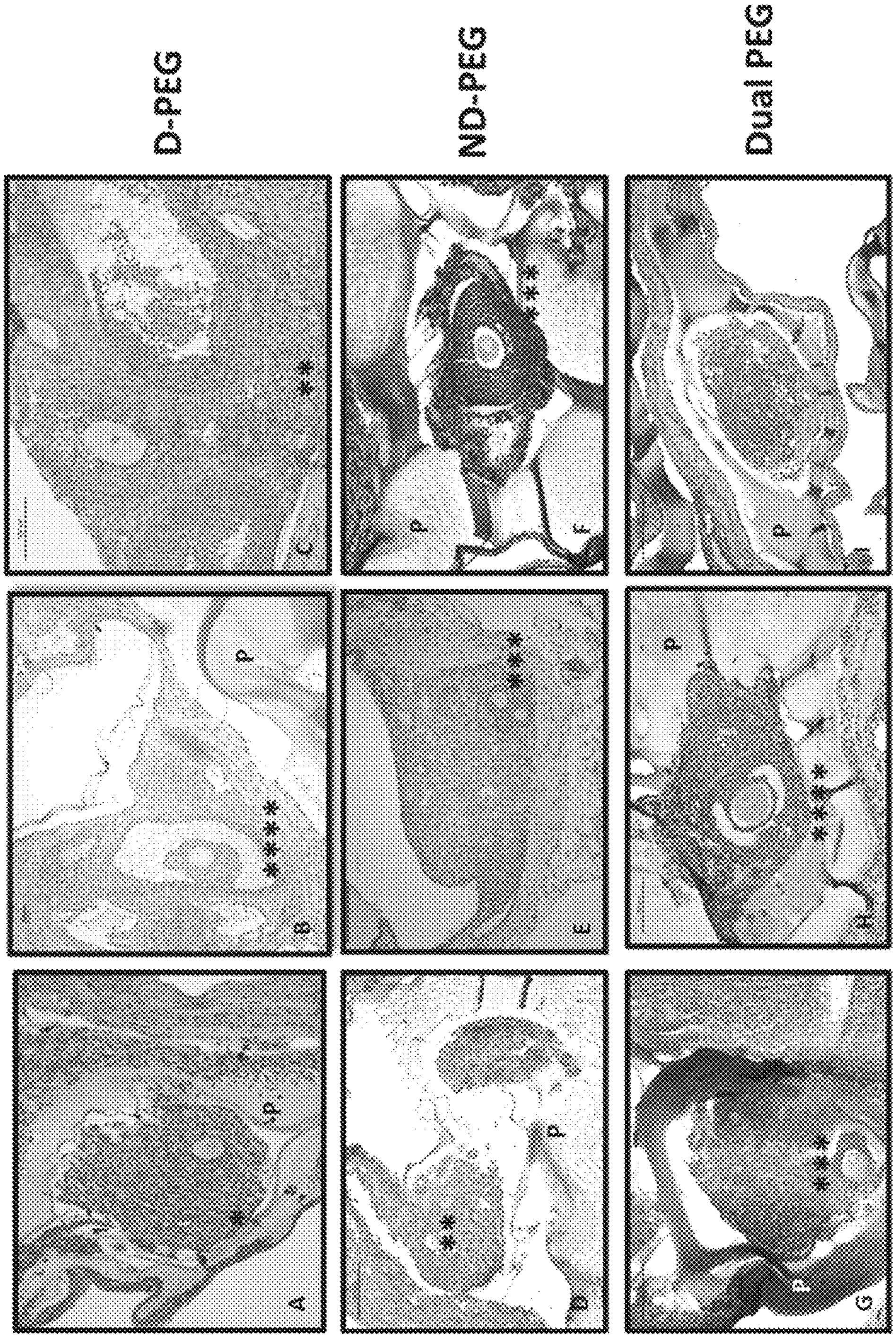
FIG. 11 is a series of histological images of ovarian tissue encapsulated in D-PEG (11A) showing primordial follicles (*) in 7 day implants; (11B), (11C) showing secondary (') and antral follicles(**) in 30 and 60 day implants respectively; ND-PEG implants showing primary and secondary follicles (11D, 11E, 11F) after 7, 30, and 60 days, respectively, and dual PEG implants showing secondary (11G) and antral (11H) follicles in 7 and 30 day implants respectively. (11I) Ovarian tissue encapsulated in dual PEG after 60 days of implantation. Magnification 10× (11D, 11E, 11H, 11I); 20× (11A, 11B, 11C, 11F, 11**G).

Further experiments were conducted to evaluate the survival of syngeneic ovarian tissue encapsulated and implanted in ovariectomized mice after 7, 30, and 60 days (FIG. 11). Histological images were acquired of ovarian tissue encapsulated in D-PEG (FIGS. 11A, 11B, 11C), ND-PEG (FIGS. 11D, 11E, 11F), and dual-PEG (FIGS. 11G, 11H, 11I).

For D-PEG implants, primordial follicles (*) were observed to form in 7-day implants (FIG. 11A). Secondary (*) and antral follicles () were observed to form in 30-day and 60-day implants respectively (FIGS. 11B, 11**C).

For ND-PEG implants, primary and secondary follicles were observed after 7, 30, and 60 days (FIG. 11D, 11E, 11F).

For dual-PEG implants, secondary (FIG. 11G) and antral (FIG. 11H) follicles were observed in 7-day and 30-day implants, respectively. Ovarian tissue remained encapsulated in dual PEG after 60 days of implantation. The ovarian tissue survived and appeared normal. Magnification 10× (FIGS. 11D, 11E, 11H, 11I); magnification 20× (FIGS. 11A, 11B, 11C, 11F, 11G).

Figure 12:
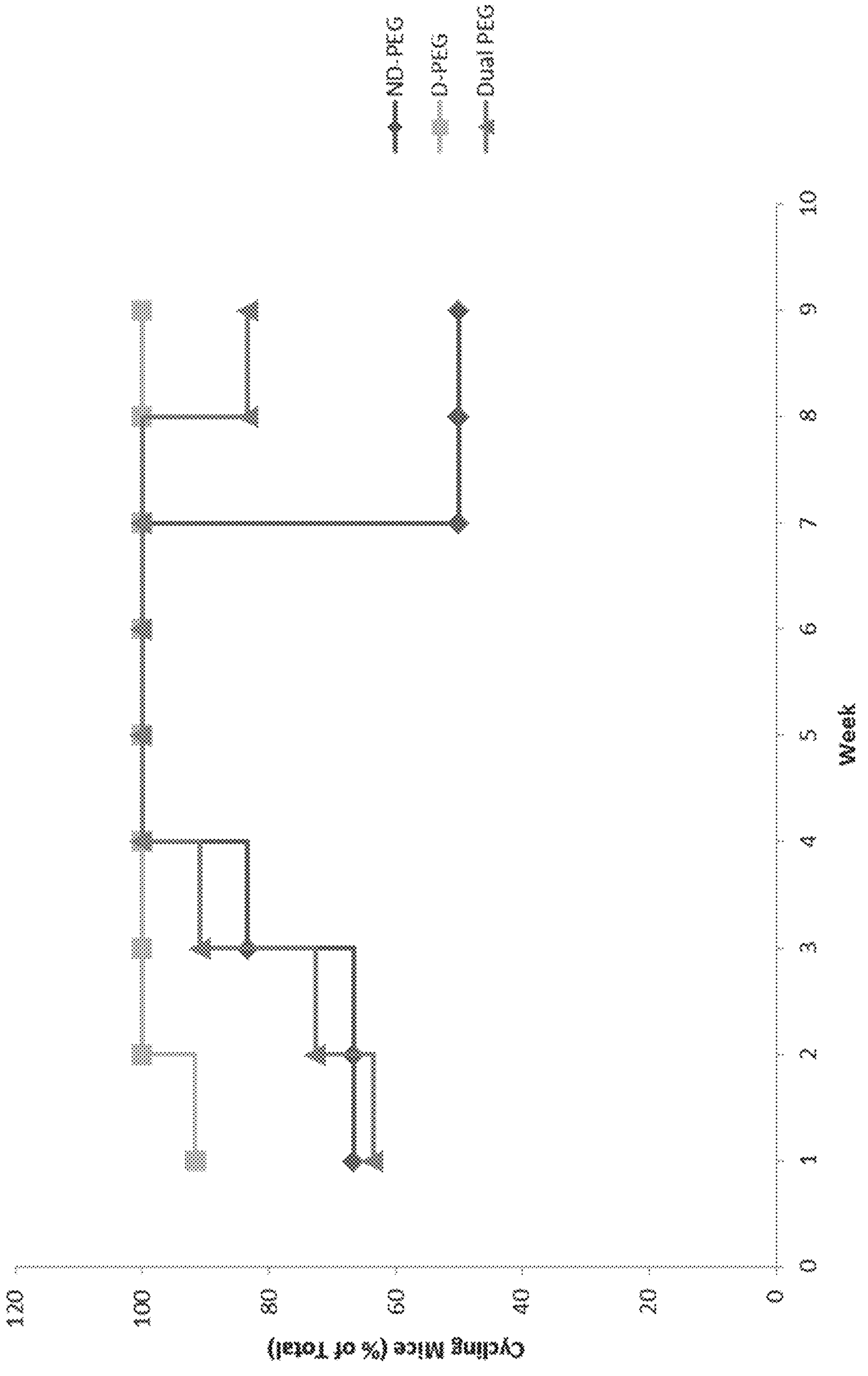
FIG. 12 is a plot showing the survival and function of encapsulated ovarian tissue. Data were collected by monitoring the frequency of the estrous cycle in mice that received tissue implanted in ND-PEG, D-PEG, and dual PEG.

Furthermore, experiments were conducted to evaluate the survival and function of encapsulated ovarian tissue by monitoring the frequency of the estrous cycle in mice that received implants. After ovariectomy, the mice cease the estrous cycle, or cyclicity, and present with continuous metestrous. Implantation of ovarian tissue that responds to circulating hormones by secreting sex hormones results in the resumption of the cyclic estrous. Estrous was observed in mice implanted with D-PEG, ND-PEG, and Dual PEG implants in the syngeneic model and the presence of cornified cells at least once per week was indicated continuation of estrus cycles (FIG. 12). The data indicated that ND-PEG implants restored estrous the least effectively of the materials tested. The dual-PEG performed restored estrous best.

Ovariectomy in mice results in removal of the sex hormones normally produced and secreted by the ovary. Estradiol is one of the hormones produced in the ovary. Follicle stimulating hormone (FSH) is secreted from the pituitary gland and stimulates the production of estradiol. A negative feedback between FSH and estradiol maintains a coordinated balance between the pituitary gland and the ovarian follicles. When the levels of estradiol decrease, the negative feedback of FSH is removed and the levels of FSH increase. Increased FSH stimulates ovaries to produce and secrete estradiol. In the absence of ovaries, as in the case of premature ovarian failure or after ovariectomy, increased levels of FSH persist. During the development of embodiments of the technology described herein, experiments produced data indicating that the FSH levels are below 15 ng/mL before ovariectomy (e.g., in healthy mice) and FSH levels reach 60 ng/mL post ovariectomy (FIG. 13A, 13B). Implantation of ovarian tissue encapsulated in D-PEG results in a decrease of FSH levels 60 days post implantation, indirectly indicating that the balance between the pituitary gland and the implanted ovarian tissue was restored (FIG. 13A). However, ND-PEG alone did not decrease the levels of FSH after 60 days (FIG. 13B), thus indicating that degradable gel provided around the implanted ovarian tissue promotes survival and function of the ovarian tissue.

Example 5—In Vivo Immunoisolation of Implanted Tissue

During the development of embodiments of the technology provided herein, experiments were conducted to evaluate hydrogels in vivo to provide immunoisolation of implanted tissue in an allogeneic mouse model. The data collected indicated that the hydrogels not only support the survival and function of the implanted allogeneic ovarian tissue (e.g., Example 4), but also that the PEG hydrogels protect the implanted tissue from inducing an immune reaction and thereby prevent rejection of the implanted tissue.

During experiments conducted during the development of embodiments of the technology provided herein, data were collected to test allogeneic transfer of tissue from one mouse to another. In particular, allogeneic ovarian tissue from Balb/C mice was isolated, encapsulated in D-PEG, and implanted in ovariectomized C57BL/6 mice. Macroscopic images of allogeneic ovarian tissue encapsulated in D-PEG and retrieved at the time of sacrifice were acquired (FIG. 14A, 14B). The data demonstrated that the implant remained positioned under the skin and the tissue was encapsulated and surrounded by the hydrogel. No evidence of rejection was observed. In control experiments, implantation of allogeneic ovarian tissue without encapsulation results in rejection and elimination of the implanted tissue after 28 days of implantation (FIG. 15). Microscope images were taken at magnification of 5× (FIG. 15A) and 20× (FIG. 15B). Analysis of the images indicated destruction of the tissue and that no ovarian follicles at any stage were present in the implanted tissue. In additional experiments that were similar to the experiments performed with syngeneic tissue implantation, ovariectomy causes cessation of the estrous cycle in mice and the mice present with continuous metestrous. Implantation of the allogeneic ovarian tissue without the immunoisolating device did not result in sustained cyclicity (FIG. 16A). In contract, estrous was observed in mice implanted with allogeneic tissue encapsulated in D-PEG (FIG. 16B), in the commercially available TheraCyte® device (FIG. 16C), and in Dual PEG (FIG. 16D) for 14 weeks post implantation.

Figure 17:
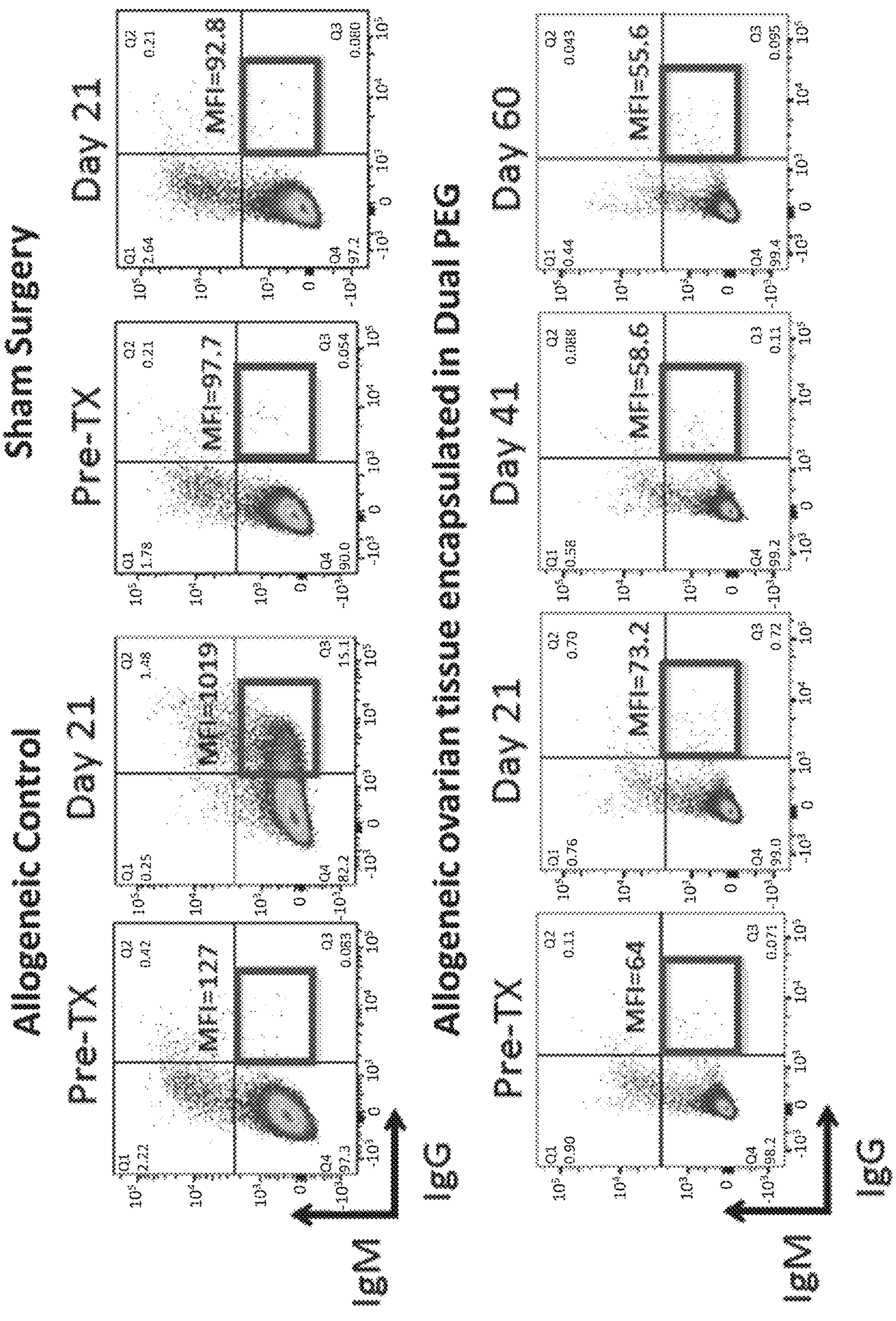
FIG. 17 shows flow cytometry data collected to evaluate the immune reaction towards the implanted allogeneic tissue without the device (allogeneic control), healthy mice without the device (sham surgery), and encapsulated tissue (allogeneic ovarian tissue encapsulated in dual PEG). Pre-TX indicates pre-implantation. Without immunoisolation, the recipients developed IgG 21 days after receiving the allograft (enclosed by the rectangle). Mice that received allograft encapsulated in dual PEG hydrogel presented no antibodies up to 60 days post implantation, similar to the negative controls. Plots were obtained and mean fluorescence intensities (MFI) in the APC-channel determined with FlowJo software. Rectangles indicate thymocytes bound to IgG.

In addition, flow cytometry analysis was used to evaluate the immune reaction towards the implanted allogeneic tissue without the device (control), healthy mice without the device (sham surgery), and encapsulated tissue (allogeneic ovarian tissue encapsulated in dual PEG) (FIG. 17). In all tested groups before implantation (Pre-TX), no IgM or IgG reactive to Balb/c were found in sera. Without immunoisolation the recipients developed IgG in approximately 21 days after receiving the allograft (highlighted with a gray square). Mice that underwent sham surgery did not develop antibodies (negative control).

Most importantly, mice that received allograft encapsulated in dual PEG hydrogel presented no antibodies up to 60 days post implantation, similar to the negative controls. In FIG. 17, plots were obtained and mean fluorescence intensities (MFI) in the APC-channel were determined with FlowJo software. Gray squares depict the fraction of thymocytes bound to IgG. Together with the cyclicity and FSH results (above), these data indicate that PEG hydrogels protect the allogeneic ovarian tissue from rejection while maintaining the survival and function of the implanted tissue.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

I claim:

1. A method of preparing an immunoisolation device, the method comprising:
   (a) providing an inner core comprising a degradable hydrogel and a biological material; and
   (b) encapsulating the inner core within an outer shell comprising a non-degradable hydrogel.

2. The method of claim 1, wherein providing the inner core comprises:
   (a) mixing a hydrogel solution with a protease degradable linker peptide to provide a degradable hydrogel precursor solution;
   (b) cross-linking the degradable hydrogel precursor solution to provide an inner core comprising a degradable hydrogel; and
   (c) implanting the biological material in the inner core.

3. The method of claim 2, wherein the degradable linker peptide has an amino acid sequence selected from a group consisting of:

```
                              (SEQ ID NO: 1)
Ac-GCYKNSGCYKNSCG;

                              (SEQ ID NO: 2)
GCYKNSGCYKNSCG; and

                              (SEQ ID NO: 3)
GCRDVPMSMRGGDRCGYKNSCG.
```

4. The method of claim 1, wherein encapsulating the inner core within an outer shell comprises:
   (a) preparing a hydrogel solution comprising a photoinitiator to provide a non-degradable hydrogel precursor solution;
   (b) placing the inner core in a bead of the non-degradable hydrogel precursor solution; and
   (c) cross-linking the non-degradable hydrogel precursor solution.

5. The method of claim 1, further comprising:
   suspending the biological material in a culture or maintenance medium prior to encapsulation; or preserving the biological material in an environment prior to encapsulation.

6. The method of claim 5, wherein the biological material is diluted into the culture or maintenance medium at a dilution of between 1:0.05 and 1:200.

7. The method of claim 5, wherein the culture or maintenance medium is selected from a group consisting of: a physiological solution (isotonic saline), a glucosate solution, a Basal Medium Eagle (BME), a Hanks salt solution, a tissue culture medium 199 (TCM 199), a phosphate buffered saline (PBS) and derivatives thereof, a Krebs salts solution, a Dulbecco modified Eagle's medium (DMEM), a tris buffered medium (TBM), a Tyrode's salts solution, a Modified sperm washing medium, a modified human tubal fluid, a Modified Ham's F-10 medium, an Upgraded B2 INRA medium, a B2 INRA Menezo Medium, and an Upgraded B9 medium.

8. The method of claim 5, wherein the environment provides a temperature between ambient room temperature and −200° C.

9. The method of claim 5, wherein the environment provides a temperature between a normal body temperature and −200° C.

10. The method of claim 5, wherein the environment provides a humidity between 40% and 100%.

11. The method of claim 1, wherein the inner core is configured to expand and contract.

12. The method of claim 1, wherein the inner core is configured to allow the biological material to grow.

13. The method of claim 1, wherein the outer shell is configured to allow exchange of metabolites with an environment outside the device and to protect the biological material from immune reaction by immune system components outside the device.

14. The method of claim 1, wherein the biological material is immunoisolated.

15. The method of claim 1, wherein the biological material comprises a cell.

16. The method of claim 15, wherein the cell is selected from a group consisting of: a somatic cell, a germ cell, a gamete, differentiated stem cell, a genetically engineered cell.

17. The method of claim 15, wherein the cell is selected from a group consisting of: a pancreatic islet, a hepatocyte, a choroid plexus, a neuron, a parathyroid cell, a cell secreting a clotting factor.

18. The method of claim 1, further comprising identifying a subject for treatment with the immunoisolation device and wherein the biological material is from an autologous source, an allogeneic source, or a xenogeneic source with respect to the subject.

19. The method of claim 1, wherein the biological material produces a bioactive substance.

20. The method of claim 19, wherein the bioactive substance is selected from a group consisting of: estrogen, androstenedione (the precursor of progesterone), and progesterone, insulin, glucagon, erythropoietin, Factor VIII, Factor IX, hemoglobin, albumin, neurotransmitters such as dopamine, gamma-aminobutyric acid (GABA), glutamic acid, serotonin, norepinephrine, epinephrine, and acetylcholine, growth factors, pain inhibitors, hormones, immunomodulators, neuromodulators, lymphokines, cytokines, cofactors, antibodies, aptamers, and enzymes.

21. The method of claim 1, wherein the outer shell comprises an internal surface contacting said inner core and an external surface contacting the environment outside the device.

22. A method of preparing an immunoisolation device, the method comprising:
   (a) cross-linking a degradable hydrogel precursor solution to provide an inner core comprising a degradable hydrogel;
   (b) implanting a biologic material in the inner core; and
   (c) encapsulating the inner core within an outer shell comprising a non-degradable hydrogel.

* * * * *

```
                              SEQUENCE LISTING


Sequence total quantity: 4
SEQ ID NO: 1            moltype = AA  length = 14
FEATURE                 Location/Qualifiers
REGION                  1..14
                        note = Synthetic peptide
source                  1..14
                        mol_type = protein
                        organism = synthetic construct
SEQUENCE: 1
GCYKNSGCYK NSCG                                                 14

SEQ ID NO: 2            moltype = AA  length = 14
FEATURE                 Location/Qualifiers
REGION                  1..14
                        note = Synthetic peptide
source                  1..14
                        mol_type = protein
                        organism = synthetic construct
SEQUENCE: 2
GCYKNSGCYK NSCG                                                 14

SEQ ID NO: 3            moltype = AA  length = 22
FEATURE                 Location/Qualifiers
REGION                  1..22
                        note = Synthetic peptide
source                  1..22
                        mol_type = protein
                        organism = synthetic construct
SEQUENCE: 3
GCRDVPMSMR GGDRCGYKNS CG                                        22

SEQ ID NO: 4            moltype = AA  length = 22
FEATURE                 Location/Qualifiers
REGION                  1..22
                        note = Synthetic peptide
source                  1..22
                        mol_type = protein
                        organism = synthetic construct
SEQUENCE: 4
GCRDVPMSMR GGDRCGYKNS CG                                        22
```